US009716241B2

(12) United States Patent
Kirner et al.

(10) Patent No.: US 9,716,241 B2
(45) Date of Patent: Jul. 25, 2017

(54) POLYCYCLIC DITHIOPHENES

(71) Applicant: BASF SE, Ludwigshafen (DE)

(72) Inventors: Hans Juerg Kirner, Basel (CH); Natalia Chebotareva, Hagenthal le Bas (FR); Olivier Frederic Aebischer, Duedingen (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/965,128

(22) Filed: Dec. 10, 2015

(65) Prior Publication Data
US 2016/0104849 A1 Apr. 14, 2016

Related U.S. Application Data

(62) Division of application No. 13/322,506, filed as application No. PCT/EP2010/057038 on May 21, 2010, now Pat. No. 9,233,930.

(30) Foreign Application Priority Data

May 27, 2009 (EP) .................................... 09161243
Sep. 14, 2009 (EP) .................................... 09170185

(51) Int. Cl.
| | | |
|---|---|---|
| C08G 75/00 | (2006.01) |
| H01L 51/00 | (2006.01) |
| C07D 233/28 | (2006.01) |
| C08G 61/12 | (2006.01) |
| C07D 495/04 | (2006.01) |
| C07D 513/14 | (2006.01) |
| C07F 7/08 | (2006.01) |
| C08F 128/06 | (2006.01) |
| C08G 75/06 | (2006.01) |
| C08G 75/32 | (2006.01) |
| H01L 51/05 | (2006.01) |

(52) U.S. Cl.
CPC ........ *H01L 51/0094* (2013.01); *C07D 233/28* (2013.01); *C07D 495/04* (2013.01); *C07D 513/14* (2013.01); *C07F 7/0814* (2013.01); *C08F 128/06* (2013.01); *C08G 61/122* (2013.01); *C08G 61/123* (2013.01); *C08G 61/126* (2013.01); *C08G 75/06* (2013.01); *C08G 75/32* (2013.01); *H01L 51/0036* (2013.01); *H01L 51/0043* (2013.01); *H01L 51/0071* (2013.01); *H01L 51/0074* (2013.01); *C08G 2261/3241* (2013.01); *C08G 2261/3243* (2013.01); *C08G 2261/3247* (2013.01); *C08G 2261/414* (2013.01); *C08G 2261/92* (2013.01); *H01L 51/0003* (2013.01); *H01L 51/0545* (2013.01); *H01L 51/0558* (2013.01); *Y02E 10/549* (2013.01)

(58) Field of Classification Search
CPC ...... C08G 2261/3223; C08G 2261/126; C08G 2261/124; C08G 2261/95; C08G 2261/91; C07D 417/14

See application file for complete search history.

(56) References Cited

U.S. PATENT DOCUMENTS

| | | |
|---|---|---|
| 2005/0104058 A1 | 5/2005 | Veres et al. |
| 2005/0193504 A1 | 9/2005 | Glenn et al. |
| 2009/0065770 A1 | 3/2009 | Miura et al. |
| 2010/0297405 A1 | 11/2010 | Flores et al. |
| 2011/0004004 A1 | 1/2011 | Hao et al. |
| 2011/0006287 A1 | 1/2011 | You et al. |
| 2011/0062426 A1 | 3/2011 | Kirner et al. |
| 2011/0186821 A1 | 8/2011 | Schaefer et al. |
| 2011/0215313 A1 | 9/2011 | Dueggeli et al. |
| 2011/0240981 A1 | 10/2011 | Dueggeli et al. |
| 2012/0153274 A1 | 6/2012 | Sonar et al. |

FOREIGN PATENT DOCUMENTS

| | | |
|---|---|---|
| EP | 2 006 291 | 12/2008 |
| WO | 03 052841 | 6/2003 |
| WO | 2005 003126 | 1/2005 |
| WO | 2009 092671 | 7/2009 |
| WO | 2009 115413 | 9/2009 |
| WO | 2010 046259 | 4/2010 |
| WO | WO 2010/136353 A1 | 12/2010 |
| WO | WO 2011/002927 A2 | 1/2011 |

OTHER PUBLICATIONS

Wiersema, A. K., et al., "Thiophene Analogues of Fluorene. IV. An Unusual Behaviour of a Cyclopentadithiophenone in the Reaction with Dienophiles," Acta Chemical Scandinavica, vol. 24, No. 7, pp. 2653-2655, (Jan. 1, 1970) XP008118237.

Letizia, J. A., et al., "n-Channel Polymers by Design: Optimizing the Interplay of Solubilizing Substituents, Crystal Packing, and Field-Effect Transistor Characteristics in Polymeric Bithiophene-Imide Semiconductors," Journal of the American Chemical Society, vol. 130, No. 30, pp. 9679-9694, (Jul. 30, 2008) XP002585890.

Tsuchimoto, T., et al., "Easy Access to Aryl- and Heteroaryl-Annulated [a] carbazoles by the Indium-Catalyzed Reaction of 2-Arylindoles with Propargyl Ethers," Angewandte Chemie. International Edition, vol. 44, pp. 1336-1340, (Jan. 1, 2005) XP002448772.

Zotti, G., et al., "Highly conjugated acrylate-functionalized polythiophenes from anodic coupling of thiophene- and bithiophene-hexyl acrylates," Synthetic Metals, vol. 105, No. 2, pp. 135-139, (Jan. 1, 1999) XP002585893.

(Continued)

*Primary Examiner* — Shane Fang
(74) *Attorney, Agent, or Firm* — Oblon, McClelland, Maier & Neustadt, L.L.P.

(57) ABSTRACT

The present invention relates to novel compounds, corresponding oligomers and (co)polymers. The compounds according to the invention are useful as semiconductors and have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics (solar cells) and photodiodes.

10 Claims, No Drawings

(56) References Cited

OTHER PUBLICATIONS

Lee, K-H., et al., "Synthesis of oligomers having a pendant dithienosilole unit and their applications to EL device materials," Journal of Organometallic Chemistry, vol. 690, No. 2, pp. 333-337, (Jan. 17, 2005) XP002585892.

Baumgartner, T., et al., "The Dithieno[3,2-b:2',3'-d]phosphole System: A Novel Building Block for Highly Luminescent pi.-Conjugated Materials," Angewandte Chemie. International Edition, vol. 43, No. 45, pp. 6197-6201, (Nov. 19, 2004) XP002585891.

Guegano, X., et al., "Pronounced Electrochemical Amphotericity of a Fused Donor-Acceptor Compound: A Planar Merge of TTF with a TCNQ-Type Bithienoquinoxaline," Chemistry—A European Journal, vol. 15, No. 1, pp. 63-66, (2009) XP008118227.

International Search Report Issued May 26, 2011 in PCT/EP10/057038 Filed May 21, 2010.

European Search Report Issued Jun. 11, 2010 in European Patent Application No. 09170185.4 Filed Sep. 14, 2009.

Office Action issued Jun. 23, 2014 in Japanese Patent Application No. 2012-512320 (submitting English translation only).

John D. Tovar, et al., "Functionalizable polycyclic aromatics through oxidative cyclization of pendant thiophenes", Journal of the American Chemical Society, vol. 124, No. 26, 2002, pp. 7762-7769.

John D. Tovar, et al., "Poly(naphthodithiophene)s: Robust, conductive electrochromics via tandem cyclization-polymerizations", Advanced Materials, vol. 13, No. 23, Dec. 3, 2001, pp. 1775-1780.

Jaclyn L. Brusso, et al., "Two-dimensional structural motif in thienoacene semiconductors: Synthesis, structure, and properties of tetrathienoanthracene isomers", Chemistry of Materials, vol. 20, No. 7, 2008, pp. 2484-2494.

Daniel M. Perrine, et al., "Four novel phenyldithienoindole isomers from the oxidative photocyclization of dithienylpyrroles", Journal of Organic Chemistry, vol. 52, No. 11, 1987, pp. 2213-2216.

Uwe Dahlmann, et al., "The diyne reaction of 3,3'-bis(phenylethynyl)-2,2'-bithiophene derivatives via rhodium complexes: A novel approach to condensed benzo[2,1-$b$:3,4-$b'$]dithiophenes", Helvetica Chimica Acta, vol. 80, No. 1, 1997, pp. 111-120.

Nimal Jayasuriya, et al., "Photocyclization of terthiophenes", Journal of Organic Chemistry, vol. 54, No. 17, 1989, pp. 4203-4205.

Shengqiang Xiao et al. "Conjugated Polymers of Fused Bithiophenes with Enhanced π-Electron Delocalization for Photovaltaic Applications", Macromolecules 2008, 41, 5688-5696.

POLYCYCLIC DITHIOPHENES

CROSS-REFERENCE TO RELATED APPLICATIONS

This application is a Divisional of U.S. application Ser. No. 13/322,506, which was filed on Dec. 21, 2011. U.S. application Ser. No. 13/322,506 is a National Phase of PCT/EP2010/057038, which was filed on May 21, 2010. This application is based upon and claims the benefit of priority to European Application No. 09161243.2, which was filed on May 27, 2009, and to European Application No. 09170185.4, which was filed on Sep. 14, 2009.

The present invention relates to novel bridged 2,2'-dithiophene derivates, oligomers and copolymers thereof, and their use as organic semiconductor in organic devices as well as to a semiconducter device comprising said bridged dithiophene derivate.

The novel compounds of the present invention generally conform to the formula I

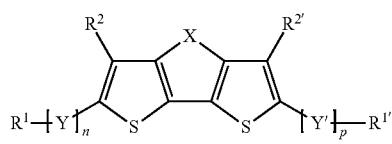

wherein $R^1$ and $R^{1'}$ independently of each other are H or a substituent, halogen or $SiR^6R^4R^5$; $R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and if $R^3$ and $R^{3'}$ within the definition of X together complete a ring structure, or X is a bridging group conforming to one of the formulae

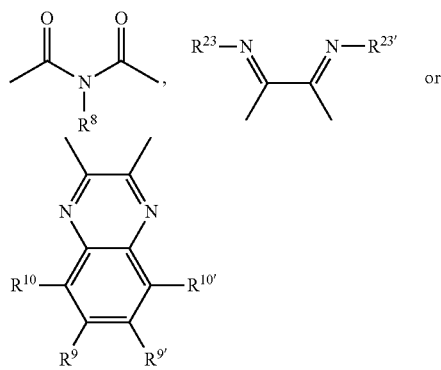

R2 and/or R2' may also be halogen or hydrogen;
Y and Y' independently are selected from

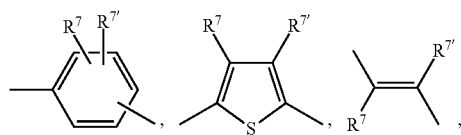

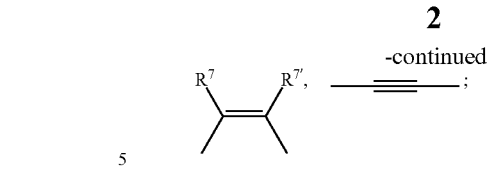

n and p independently range from 0 to 6.

$R^4$, $R^5$, $R^6$ independently are selected from $C_1$-$C_{25}$alkyl, $C_3$-$C_{12}$cycloalkyl, $C_4$-$C_{25}$aryl, or $C_5$-$C_{25}$aralkyl; and the neighbouring residues $R^4$ and $R^5$ may further be interlinked to form a divalent hydrocarbon residue of 4 to 25 carbon atoms which may be substituted and/or interrupted;

$R^7$ and $R^{7'}$ independently are H or a substituent; or vicinal $R^7$ and $R^{7'}$ together, with the carbon atoms they are attached to, complete a 5-membered unsubstituted or substituted heterocyclic ring comprising at least one hetero atom selected from N, O, S.

In one variation of the present compounds, X is the divalent linking group

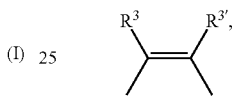

where $R^3$ and $R^{3'}$ independently are hydrogen or a substituent, or are amino, or together, with the carbon atoms they are attached to, complete a 5- or 6-membered unsubstituted or substituted hydrocarbon ring, or a 5-membered unsubstituted or substituted heterocyclic ring comprising at least one hetero atom selected from N, O, S, where any substituent, if present, is as defined below.

Another embodiment comprises a linking group X whose $R^3$ and $R^{3'}$ together form a bridging group

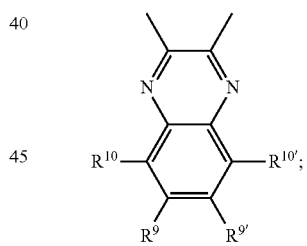

where neighbouring residues $R^9$ and $R^{9'}$, or $R^9$ and $R^{10}$ and/or $R^{9'}$ and $R^{10'}$, together, with the carbon atoms they are attached to, complete a 5-membered unsubstituted or substituted heterocyclic ring comprising at least one hetero atom selected from N, O, S.

A further embodiment comprises a linking group X conforming to the formula

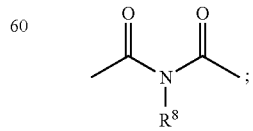

wherein $R^8$ is substituted $C_4$-$C_{10}$aryl, $C_1$-$C_{19}$heteroaryl, or to the formula

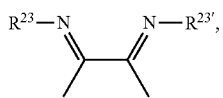

where $R^{23}$ and $R^{23'}$ each is a substituent, especially alkyl, OH or alkoxy. $R^8$ as aryl or heteroaryl may optionally be attached via divalent organic linking group L as defined further below.

Any substituent, where present in the compounds including oligomers, polymers or copolymers of the invention, generally is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$heterocycloalkyl, $C_1$-$C_{25}$acyloxy; or is selected from the residues COR, CH═NR, CH═N—OH, CH═N—OR, COOR, CONHR, CONRR', CONH—NHR, CONH—NRR', SO$_2$R, SO$_3$R, SO$_2$NHR, SO$_2$NRR', SO$_2$NH—NHR, SO$_2$NH—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, NO$_2$, NHR, NRR', NH—NHR, NH—NRR', CONROH; and if bonding to non-aromatic carbon or to sulphur, may also be oxo; R, R' and R" independently are selected from $C_1$-$C_{25}$alkyl, $C_1$-$C_{25}$haloalkyl, $C_5$-$C_{10}$aryl, $C_3$-$C_{12}$cycloalkyl, preferably from $C_1$-$C_6$alkyl, phenyl, cyclopentyl, cyclohexyl; and R may also be hydrogen; where each substituent, or R, R' and R", which is $C_4$-$C_{10}$aryl or $C_1$-$C_9$heteroaryl, itself is unsubstituted or substituted by $C_1$-$C_4$alkyl, $C_2$-$C_4$alkenyl, $C_1$-$C_4$alkoxy, CHO, $C_1$-$C_4$alkylcarbonyl, $C_2$-$C_4$alkenyl-carbonyloxy, allyloxy, halogen. Especially preferred substituents are selected from halogen, $C_1$-$C_{25}$alkyl, SiRR'R", vinyl, allyl, phenyl; and if bonding to non-aromatic carbon or to sulphur, may also be oxo; and where R, R', R" independently are selected from $C_1$-$C_8$alkyl, phenyl, and R may also be hydrogen; and where each phenyl is unsubstituted or substituted by $C_1$-$C_4$alkyl, $C_1$-$C_4$alkoxy, CHO, vinyl, allyl, allyloxy, acryloyloxy, methacryloyloxy, halogen. Neighbouring substituents may be linked together by a carbon-carbon single bond or double bond to form an annelated carbocyclic or heterocyclic ring system.

The present compounds may also be linked together to form dimers, so in compounds wherein $R^3$ and $R^{3'}$ together, with the carbon atoms they are attached to, complete a 5-membered substituted heterocyclic ring comprising at least one hetero atom selected from N, O, S, where one substituent is a moiety of the formula

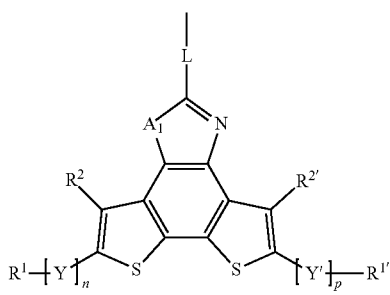

(IV)

where L stands for a divalent organic linking group, such as alkylene (e.g. $C_2$-$C_{12}$), phenylene, cycloalkylene; $A_1$ is a divalent moiety O, S, NR;

or $R^3$ and $R^{3'}$ together form a bridging group

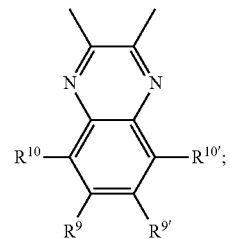

wherein the neighbouring residues $R^9$ and $R^{10}$, and $R^{9'}$ and $R^{10'}$, together with the carbon atoms they are attached to, complete a 5-membered unsubstituted or substituted thiophene ring, i.e. $R^9$ and $R^{10}$ being

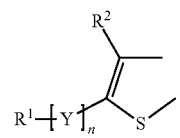

and $R^{9'}$ and $R^{10'}$ together being

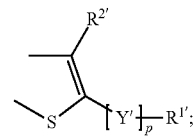

or $R^8$ is a moiety of the formula V

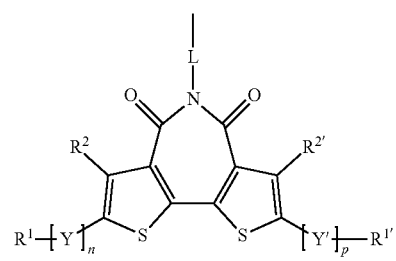

(V)

where all other symbols are as defined further above.

More specifically, the present invention relates to compounds of the formula I

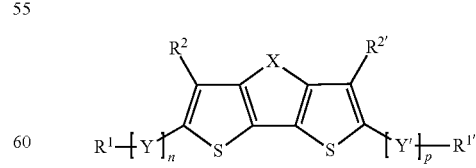

(I)

wherein
$R^1$ and $R^{1'}$ are independently of each other H, halogen or SiR$^6$R$^4$R$^5$;
$R^2$ and $R^{2'}$ may be the same or different and are selected from halogen, hydrogen, $C_1$-$C_{25}$alkyl, $C_2$-$C_{25}$alkenyl, $C_2$-$C_{25}$alkynyl, $C_5$-$C_{12}$cycloalkyl, $C_4$-$C_{25}$aryl, $C_5$-$C_{25}$alkylaryl or $C_5$-$C_{25}$aralkyl, each of which is unsubstituted or substituted;

X is selected from

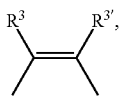

wherein $R^3$ and $R^{3'}$ together form a cyclic structure as defined, and

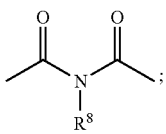

Y and Y' independently are selected from

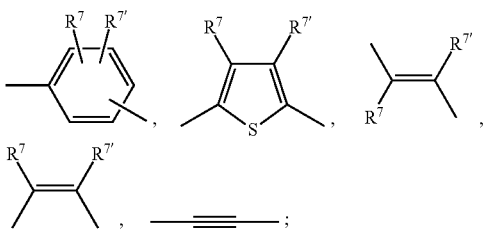

n and p independently range from 0 to 6, with the range from 0 to 3 being preferred;

R4, R5, R6 independently are selected from $C_1$-$C_{12}$alkyl, $C_5$-$C_{12}$cycloalkyl, phenyl, or $C_7$-$C_{12}$phenylalkyl;

$R^7$ and $R^{7'}$ independently are H or a substituent; or vicinal $R^7$ and $R^{7'}$ together, with the carbon atoms they are attached to, complete a 5-membered unsubstituted or substituted heterocyclic ring comprising at least one hetero atom selected from N, O, S;

$R^8$ is substituted $C_4$-$C_{10}$aryl, $C_1$-$C_{19}$heteroaryl;

$R^9$, $R^{9'}$, $R^{10}$ and $R^{10'}$ independently are hydrogen or a substituent; or neighbouring residues $R^9$ and $R^{9'}$, or $R^9$ and $R^{10}$ and/or $R^{9'}$ and $R^{10'}$, together, with the carbon atoms they are attached to, complete a 5-membered unsubstituted or substituted heterocyclic ring comprising at least one hetero atom selected from N, O, S; and any substituent, if present, is selected from halogen, OR, $C_1$-$C_{25}$alkyl, $C_2$-$C_{25}$alkenyl, $C_1$-$C_{25}$alkylthio, $C_1$-$C_{25}$acyl, $C_4$-$C_{10}$aryl, $C_1$-$C_9$heteroaryl, $C_3$-$C_{12}$cycloalkyl, $C_2$-$C_{11}$heterocycloalkyl, $C_1$-$C_{25}$acyloxy, $C_5$-$C_{10}$aryloxy, $C_5$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', PO(OR)$_2$, PO(NHR)$_2$, PO(NRR')$_2$, CN, $NO_2$, NHR, NRR', NH—NHR, NH—NRR', CONROH; and if bonding to non-aromatic carbon or to sulphur, may also be oxo; and where R, R' and R" independently are selected from $C_1$-$C_{18}$alkyl, phenyl, cyclopentyl, cyclohexyl; and R may also be hydrogen; and where each substituent, or R, R' and R", which is $C_4$-$C_{10}$aryl, phenyl, $C_1$-$C_9$heteroaryl, itself is unsubstituted or substituted by $C_1$-$C_4$alkyl, $C_2$-$C_4$alkenyl, $C_1$-$C_4$alkoxy, CHO, $C_1$-$C_4$alkyl-carbonyl, $C_2$-$C_4$alkenyl-carbonyloxy, allyloxy, halogen, while any neighbouring substituents may be linked together by a carbon-carbon single bond or double bond.

The present compounds of the formula I may conveniently be converted into oligomers or polymers following methods known in the art such as Suzuki-polymerization or copolymerization, or radical (co)polymerization of compounds of the formula I which contain a polymerizable ethylenically unsaturated group.

The compounds of the invention thus also comprise oligomers, polymers and copolymers comprising at least 2 structural units of the formula II'

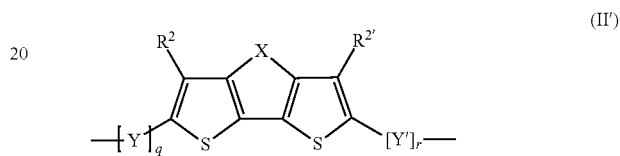

or of the formula III'

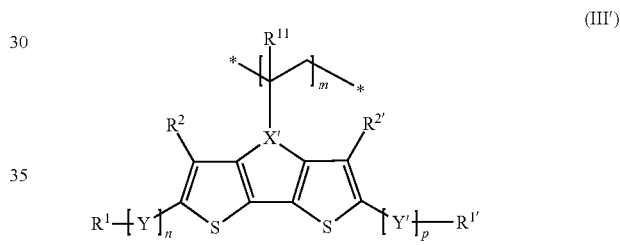

wherein $R^1$, $R^{1'}$, $R^2$, $R^{2'}$, Y, Y', p and n are as defined above;

m denotes the number of structural units of formula III in the oligomer or (co)polymer, which preferably ranges from 2 to about 50000;

X is a divalent linking group

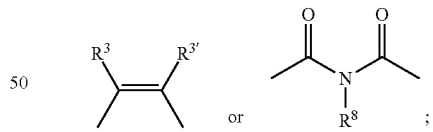

X' is a trivalent linking group which is derived, together with the moiety integrated into the chain, from

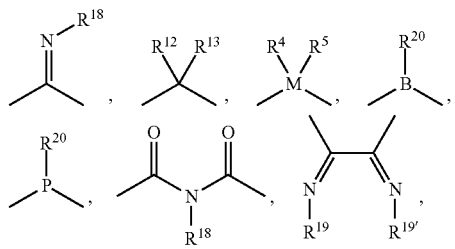

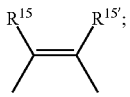

M is Si or Ge;

R$^3$ and R$^{3'}$, R$^{15}$ and R$^{15'}$, independently, are hydrogen or a substituent, or together with the carbon atoms they are attached to complete a 5- or 6-membered unsubstituted or substituted hydrocarbon ring, or a 5-membered unsubstituted or substituted heterocyclic ring comprising at least one hetero atom selected from N, O, S, where any substituent, if present, is as defined below;

or R$^3$ and R$^{3'}$, or R$^{15}$ and R$^{15'}$, together form a bridging group

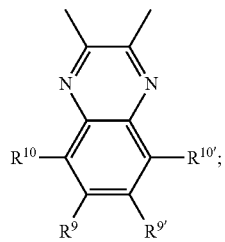

R$^4$, R$^5$ independently are selected from C$_1$-C$_{25}$alkyl, C$_3$-C$_{12}$cycloalkyl, C$_4$-C$_{25}$aryl, or C$_5$-C$_{25}$aralkyl, which may further be interlinked to form a divalent hydrocarbon residue of 4 to 25 carbon atoms which may be substituted and/or interrupted;

R$^8$ is substituted C$_4$-C$_{10}$aryl, C$_1$-C$_{19}$heteroaryl; R$^9$, R$^{9'}$, R$^{10}$ and R$^{10'}$ independently are hydrogen or a substituent; or neighbouring residues R$^9$ and R$^{9'}$, or R$^9$ and R$^{10}$ and/or R$^{9'}$ and R$^{10'}$, together, with the carbon atoms they are attached to, complete a 5-membered unsubstituted or substituted heterocyclic ring comprising at least one hetero atom selected from N, O, S; R$^{11}$ is H or methyl;

one of R12 and R13 may be hydrogen while the other, or both R12 and R13, are substituents; or both R12 and R13 are interlinked to form a divalent hydrocarbon residue of 2 to 25 carbon atoms which may be substituted and/or interrupted;

q is 0, 1, 2, 3 or 4, and R$^{14}$ is a substituent, or 2 or 3 neighbouring residues R$^{14}$ may be interlinked to form a divalent or trivalent hydrocarbon residue of 4 to 25 carbon atoms which may be substituted and/or interrupted;

R$^{16}$ and R$^{16'}$ independently are hydrogen or a substituent; R$^{18}$ is a substituent, or is substituted C$_4$-C$_{10}$aryl, C$_1$-C$_{19}$heteroaryl;

R$^{19}$ and R$^{19'}$ together form a bridging group selected from

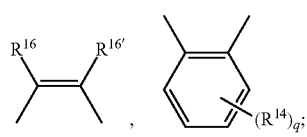

R$^{20}$ is C$_1$-C$_{25}$alkyl, C$_3$-C$_{12}$cycloalkyl, C$_4$-C$_{25}$aryl, C$_5$-C$_{25}$alkylaryl or C$_5$-C$_{25}$aralkyl, each of which is unsubstituted or substituted;

where X' contains one of R$^4$, R$^5$, R$^9$, R$^{9'}$, R$^{10}$, R$^{10'}$, R$^{12}$, R$^{13}$, R$^{14}$, R$^{14'}$, R$^{18}$, R$^{19}$, R$^{19'}$, R$^{20}$ comprising a substituent, which contains a polymerizable ethylenic double bond;

and any further substituent, if present, is as defined in accordance with formula I. The moiety integrated into the (oligo- or polymer-) chain is the moiety >C(R11)-CH$_2$—, part of the above formula III'. Consequently, the substituent comprising the polymerizable ethylenic double bond usually contains a group of the formula PG:

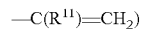

or is identical with said group; upon conversion into the oligomer or (co)polymer of the formula III', PG reacts to become a part of the oligo/polymer main chain of the formula PG':

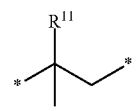

(PG'; asterisks mark linkage to said main chain).

Preferred oligomers, polymers and copolymers of the invention are those whose characterizing structural units of the above formula II' or III' share the features of preferred compounds of the formula I (see, e.g., formula II or III further below).

Some preferred compounds of the formula III' contain a bridging group X', which is derived, together with the moiety integrated into the chain, from

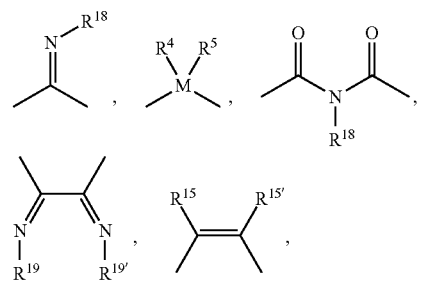

where M is Si, and other symbols are as defined.

An especially preferred set of compounds of the formula III' contains a bridging group X', which is as defined for X, with one substituent comprising a polymerizable ethylenic double bond.

End groups of the oligomers or polymers mainly depend on the method of polymerization chosen; they are usually as defined for R1 and R1' above, or may be hydrogen or alkyl, or unsaturated variants containing a unit PG rather than PG' forming the end of the polymer chain in case of formula III'. Besides the above structural units of the formula II' or III', oligomers or polymers of the invention may contain further monomer units, especially those useful for the preparation of electroconductive or semiconductive polymers. The polymerization starting from suitable monomers may be effected in analogy to reactions described in WO08/000664. Classes of suitable comonomer units, such as dithiophene, and branching units, as well as methods for copolymerization, are likewise described in WO08/000664 (see pages 5-26 therein).

Specific oligomeric or (co)polymeric compounds of the invention are those wherein X' is a trivalent linking group selected from

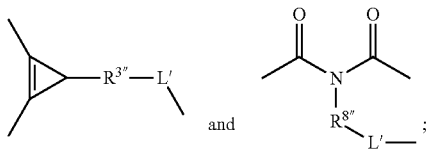

R$^{3''}$ stands for 3 atoms comprising at least one hetero atom selected from N, O, S and completing, together with the carbon atoms it is attached to, a 5-membered heterocyclic ring which may carry a further substituent, or a bridging group

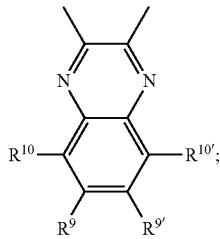

R$^{8''}$ is C$_6$-C$_{12}$arylene, C$_1$-C$_{19}$heteroarylene, each of which may carry a further substituent;
R$^9$, R$^{9'}$, R$^{10}$ and R$^{10'}$ independently are hydrogen or a substituent; or
neighbouring residues R$^9$ and R$^{9'}$, or R$^9$ and R$^{10}$ and/or R$^{9'}$ and R$^{10'}$, together, with the carbon atoms they are attached to, complete a 5-membered unsubstituted or substituted heterocyclic ring comprising at least one hetero atom selected from N, O, S; and where one of R$^9$, R$^{9'}$, R$^{10}$ and R$^{10'}$ is a chemical bond to L' or, in case that L' is a bond, together with L' forms one chemical single bond;
and L' stands for a bond or a divalent organic linking group, typically of the formula (X$_3$-D)$_{x11}$-X$_2$, wherein x11 is 0 or 1; X$_3$, X$_2$ independently are O, C$_1$-C$_4$alkylene-O, S, C$_1$-C$_4$alkylene-S, NR22, C$_1$-C$_4$alkylene-NR22, COO, C$_1$-C$_4$alkylene-COO or C$_1$-C$_4$alkylene-OCO, CONR22, C$_1$-C$_4$alkylene-CONR22 or C$_1$-C$_4$alkylene-NR22CO, NR22CONR22, C$_1$-C$_4$alkylene-NR22CONR22, C$_1$-C$_4$alkylene, or a direct bond, and D is C$_1$-C$_{24}$alkylene, C$_3$-C$_{24}$alkylene interrupted by O or COO or S, C$_2$-C$_{24}$alkenylene, C$_2$-C$_{24}$alkynylene, C$_6$-C$_{10}$arylene; where L' is especially selected from C$_6$-C$_{12}$arylene such as phenylene, C$_1$-C$_{19}$heteroarylene, C$_1$-C$_8$alkylene, C$_3$-C$_{12}$cycloalkylene, and, if attached to R$^{8''}$, a direct bond.

In a preferred oligomer or (co)polymer according to the invention,
R$^{8''}$ is phenylene or thienylene, each of which may carry a further substituent;
R$^9$, R$^{9'}$, R$^{10}$ and R$^{10'}$ independently are hydrogen; and one of R$^9$, R$^{9'}$, R$^{10}$ and R$^{10'}$ is a chemical bond to L' or, in case that L' is a bond, together with L' forms one chemical single bond;
and L' stands for a bond or a divalent organic linking group selected from C$_6$-C$_{12}$arylene, C$_1$-C$_{19}$heteroarylene, C$_1$-C$_8$alkylene, C$_3$-C$_{12}$cycloalkylene, especially from C$_1$-C$_4$alkylene, phenylene, and a chemical bond.

If comonomers are used in the preparation of compounds of the present invention (e.g. in the preparation of oligomers or copolymers), these are preferably not diketopyrrolopyrroles. Compounds of the present invention thus preferably do not contain (repeating) unit(s) of the formula

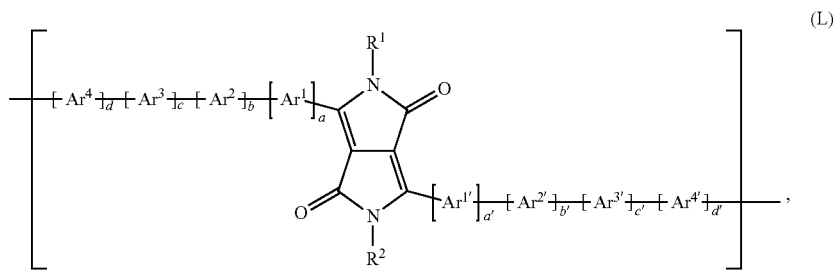

(L)

wherein a in formula L is 1, 2, or 3; a' in formula L is 0, 1, 2, or 3; b in formula L is 0, 1, 2, or 3; b' in formula L is 0, 1, 2, or 3; c in formula L is 0, 1, 2, or 3; c' in formula L is 0, 1, 2, or 3; d in formula L is 0, 1, 2, or 3; d' in formula L is 0, 1, 2, or 3;
R$^1$ and R$^2$ in formula L may be the same or different and are selected from hydrogen, a C$_1$-C$_{100}$alkyl group, —COOR$^{103}$, a C$_1$-C$_{100}$alkyl group which is substituted by one or more halogen atoms, hydroxyl groups, nitro groups, —CN, or C$_6$-C$_{18}$aryl groups and/or interrupted by —O—, —COO—, —OCO—, or —S—; a C$_7$-C$_{100}$arylalkyl group, a carbamoyl group, C$_5$-C$_{12}$cycloalkyl, which can be substituted one to three times with C$_1$-C$_8$alkyl and/or C$_1$-C$_8$alkoxy, a C$_6$-C$_{24}$aryl group, in particular phenyl or 1- or 2-naphthyl which can be substituted one to three times with C$_1$-C$_8$alkyl, C$_1$-C$_8$thioalkoxy, and/or C$_1$-C$_8$alkoxy, or pentafluorophenyl,
R$^{103}$ in formula L is C$_1$-C$_{50}$alkyl, especially C$_4$-C$_{25}$alkyl;

$Ar^1$ and $Ar^{1'}$ in formula L are independently of each other

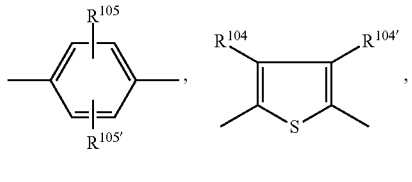

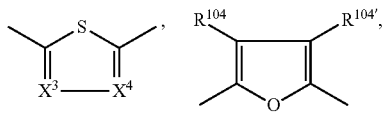

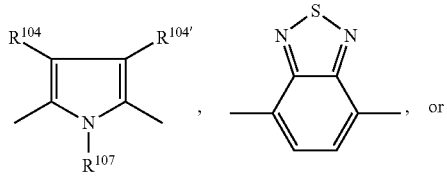

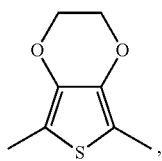

$Ar^2$, $Ar^{2'}$, $Ar^3$, $Ar^{3'}$, $Ar^4$ and $Ar^{4'}$ in formula L have the meaning of $Ar^1$ in formula L, or are independently of each other

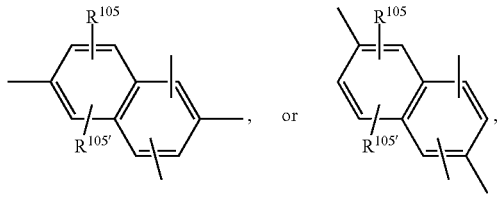

wherein one of $X^3$ in formula L and $X^4$ in formula L is N and the other is $CR^{99}$, $R^{99}$, $R^{104}$ and $R^{104'}$ in formula L are independently of each other hydrogen, halogen, especially F, or a $C_1$-$C_{25}$alkyl group, especially a $C_4$-$C_{25}$alkyl, which may optionally be interrupted by one or more oxygen or sulphur atoms, $C_7$-$C_{25}$arylalkyl, or a $C_1$-$C_{25}$alkoxy group, $R^{105}$ and $R^{105'}$ in formula L independently of each other hydrogen, halogen, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ in formula L is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

The present invention includes a polymer obtainable by homopolymerization of a compound of the formula IV

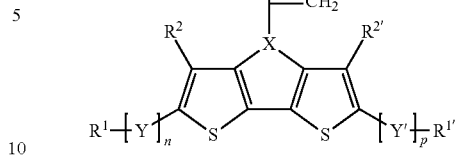

(IV)

wherein all symbols are as defined in claims 5-7, or by copolymerization of a compound of the formula IV with a suitable further monomer.

Suitable comonomers are, for example, those described in WO 09/092671, especially those bearing a functionality such as a (phosphorescent/electroluminescent) light emitting moiety (monomer $A_1$, formulae I, II, I' and I" of said WO 09/092671, see e.g. page 14, lines 15-29; page 15, lines 6-16; and specifically page 17, line 22, to page 23, line 1; page 48 line 17 to page 51; examples 1.10, 1.11, 1.12, 1.16, 1.18, 1.19, 1.20), host functionality (monomer $A_2$, see specifically page 23, line 3, to page 33, line 19, and examples 2.2, 2.4, 2.5, 2.7, 2.9, 2.10, 2.11, 2.12 of said WO 09/092671), electron transport functionality (monomer $A_3$ of said WO 09/092671, page 33, line 21, to page 37, line 2; examples 3.2, 3.4, 3.5, 3.7, 3.8, 3.9), hole transport functionality (monomer $A_4$ of said WO 09/092671, page 37, line 4, to page 45, line 2; examples 4.2, 4.3, 4.4, 4.6), and/or further structural units such as described as monomer $A_5$ of said WO 09/092671 from page 45, line 4, to page 46, line 1 (specifically examples 5.1, 5.2, 5.3, 5.4, 5.5). The above passages of WO 09/092671 are hereby incorporated by reference.

Examples for useful comonomers thus include:

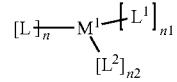

1) Compounds of the formula (2):

where in formula (2)

n=1,2 or 3;

n1=0, 1 or 2;

n2=0, 1 or 2;

$M^1$ is a metal atom of atomic weight>40, especially Ir, Pd, Pt, Rh, Re;

each of L and $L^1$ is a monodentate ligand or a bidentate ligand;

$L^2$ is a monodentate ligand; and at least one of L, $L^1$ and $L^2$ contains a polymerizable aliphatic or aromatic momomer moiety.

2) Compounds providing host functionality as described in WO07/090773, especially selected from those of the formulae

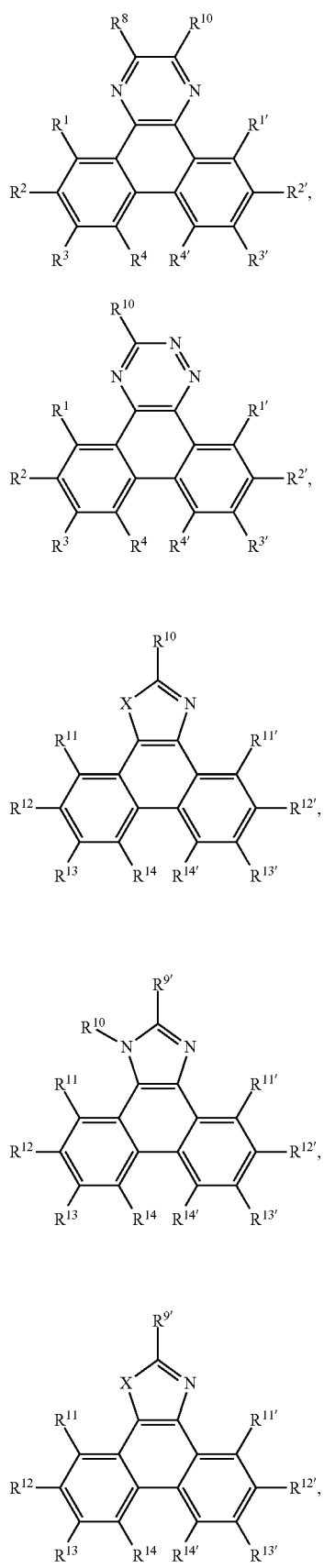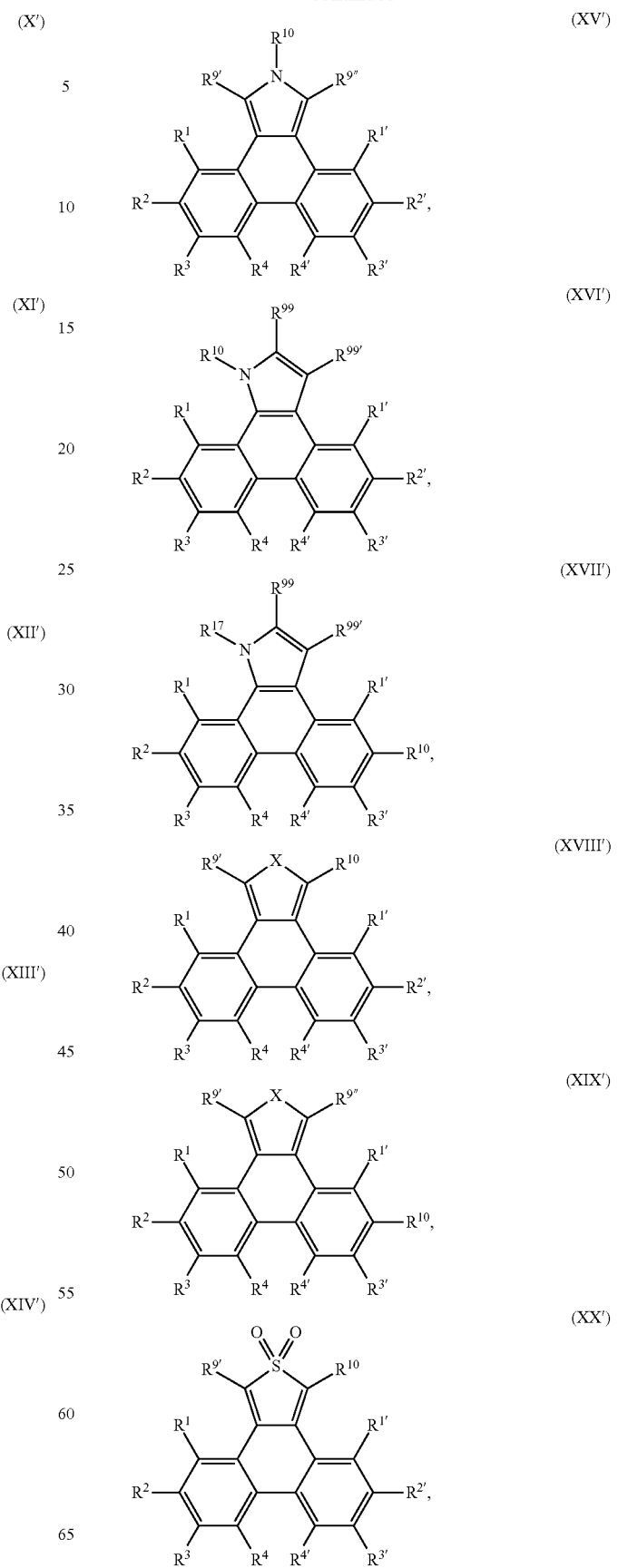

-continued

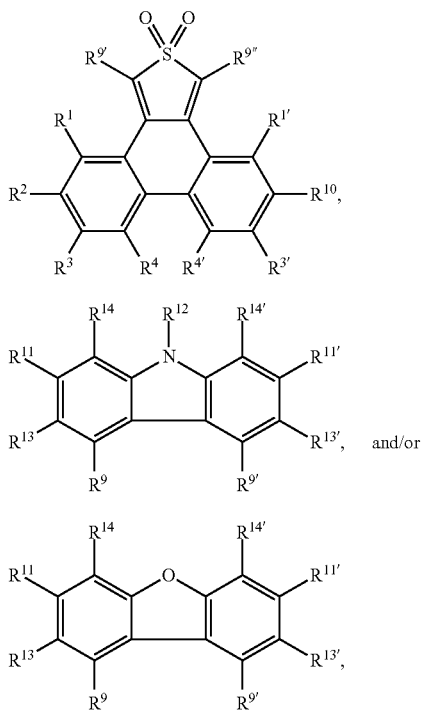

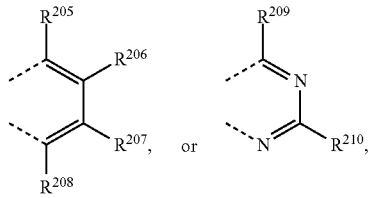

wherein

R¹ and R¹' are independently of each other hydrogen, halogen, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, R², R³, R⁴, R²', R³' and R⁴', are independently of each other H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, R⁸ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, R⁹, R⁹', R⁹'', R⁹⁹ and R⁹⁹' is H, $C_1$-$C_{18}$alkyl, $R_{10}$, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R'', GeRR'R'', POAr₂, PAr₂, or is —CO—$R^{28}$;

R¹⁰ is a group -(Sp)$_{x10}$-[PG']<, wherein Sp is a spacer unit, PG' is a group derived from a polymerisable group, with preferences as described above, and x10 is 0, or 1, or R⁸ and R¹⁰ together form a group wherein one of the substituents $R^{205}$, $R^{206}$, $R^{207}$ and $R^{208}$, and one of the substituents $R^{209}$ and $R^{210}$ is a group $R^{10}$ and the other substituents are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, R¹¹ and R¹¹' are independently of each other hydrogen, halogen, especially fluorine, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $R^{10}$, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, SiRR'R'', GeRR'R'', POAr₂, PAr₂;

R¹², R¹³, R¹⁴, R¹²'; R¹³' and R¹⁴' are independently of each other H, halogen, especially fluorine, $C_1$-$C_{18}$alkyl, $R_{10}$, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, and R¹³, R¹⁴, R¹³' and R¹⁴' may also be SiRR'R'', GeRR'R'', POAr₂, PAr₂;

X is O, S, or NR¹⁷, wherein R¹⁷ is $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, or —CO—$R^{28}$;

or two substituents R¹, R², R³ and R⁴; R¹', R²', R³' and R⁴'; R⁹, R¹¹, R¹², R¹³ and R¹⁴; R⁹', R¹¹', R¹²', R¹³' and R¹⁴', which are adjacent to each other, together form a group

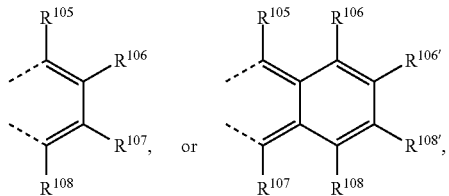

or two substituents R⁹⁹ and R⁹⁹', which are adjacent to each other, together form a group

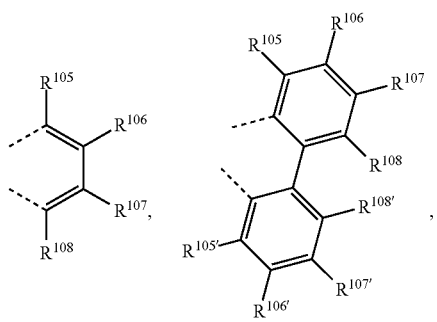

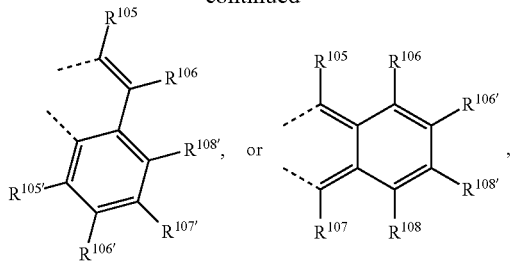

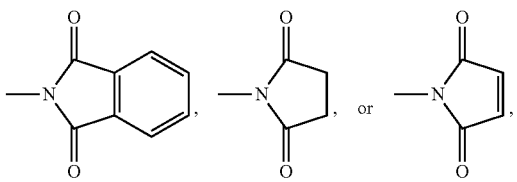

or two substituents R⁴ and R⁴', and/or R¹⁴ and R¹⁴', which are adjacent to each other, together form a group

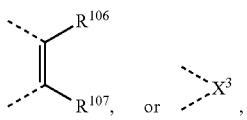

wherein $X^3$ is O, S, $C(R^{119})(R^{120})$, or $NR^{17}$, wherein $R^{17}$ is as defined above, $R^{105}$, $R^{106}$, $R^{107}$, $R^{108}$, $R^{105'}$, $R^{106'}$, $R^{107'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{120}$ together form a group of formula $=CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $-C(=O)-R^{127}$, and $R^{127}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—; —COO—; —S—; —SO—; —SO₂—; —O—; —NR²⁵—; —SiR³⁰R³¹—; —POR³²—; —CR²³=CR²⁴—; or —C≡C—; and E is —OR²⁹; —SR²⁹; —NR²⁵R²⁶; —COR²⁹; —COOR²⁷; —CONR²⁵R²⁶; —CN; or halogen; G is E, $C_1$-$C_{18}$alkyl, $C_1$-$C_{18}$alkyl which is interrupted by D, $C_1$-$C_{18}$perfluoroalkyl, or $C_1$-$C_{18}$alkoxy which is substituted by E and/or interrupted by D, wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, in particular $R^{27}$ and $R^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, R, R' and R" independently are selected from $C_1$-$C_{12}$alkyl, $C_1$-$C_{12}$haloalkyl, $C_5$-$C_{10}$aryl, $C_3$-$C_{12}$cycloalkyl, preferably from $C_1$-$C_6$alkyl, phenyl, cyclopentyl, cyclohexyl; and Ar independently is selected from $C_5$-$C_{10}$aryl, especially phenyl;

x1 is 0, or 1, with the proviso that in case of the moieties of the formulae XIV' and XXII' and XXIII' at least one of the substituents $R^{11}$, $R^{13}$, $R^{14}$, $R^{9'}$, $R^{13'}$ and $R^{14'}$ or, if present, of the substituents $R^9$, $R^{12}$ and $R^{12'}$, is a polymerizable aliphatic or aromatic momomer moiety.

3) Monomers providing electron-injection or electron-transport functionality containing a group $HEI^{II}$, which bonds to a polymerizable aliphatic or aromatic momomer moiety either directly or over a divalent spacer such as $C_1$-$C_{12}$alkylene or phenylene, and increases the electron-injection or electron-transport properties. Preferred groups $HEI^{II}$ are:

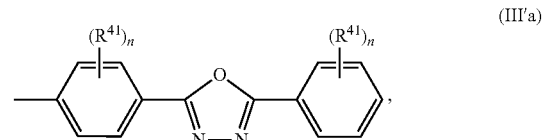

(III'a)

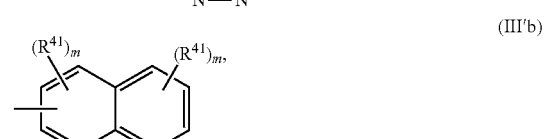

(III'b)

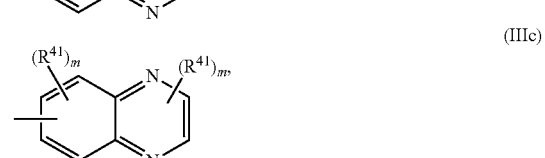

(IIIc)

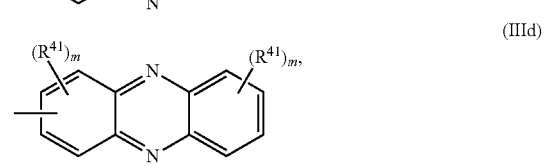

(IIId)

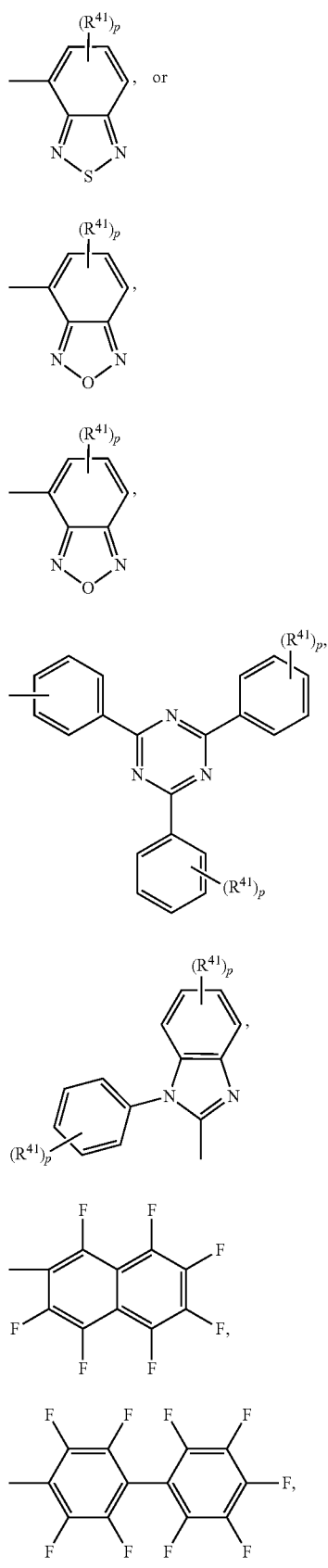

wherein $R^{42'}$ is H or $R^{41}$, $R^{41}$ can be the same or different at each occurence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by $-NR^{45}-$, $-O-$, $-S-$, $-C(=O)-O-$, or $-O-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is as defined below (item 4), and mainly comprises H or $C_1$-$C_8$alkyl;

m can be the same or different at each occurence and is 0, 1, 2, or 3, especially 0, 1, or 2, very especially 0 or 1;

n can be the same or different at each occurence and is 0, 1, 2, or 3, especially 0, 1, or 2, very especially 0 or 1;

p is 0, 1, or 2, especially 0 or 1.

4) Monomers providing hole-transport functionality containing a group HEI$^I$, which bonds to a polymerizable aliphatic or aromatic momomer moiety either directly or over a divalent spacer such as $C_1$-$C_{12}$alkylene or phenylene, and increases the hole-transport properties. Preferred groups HEI$^I$ are:

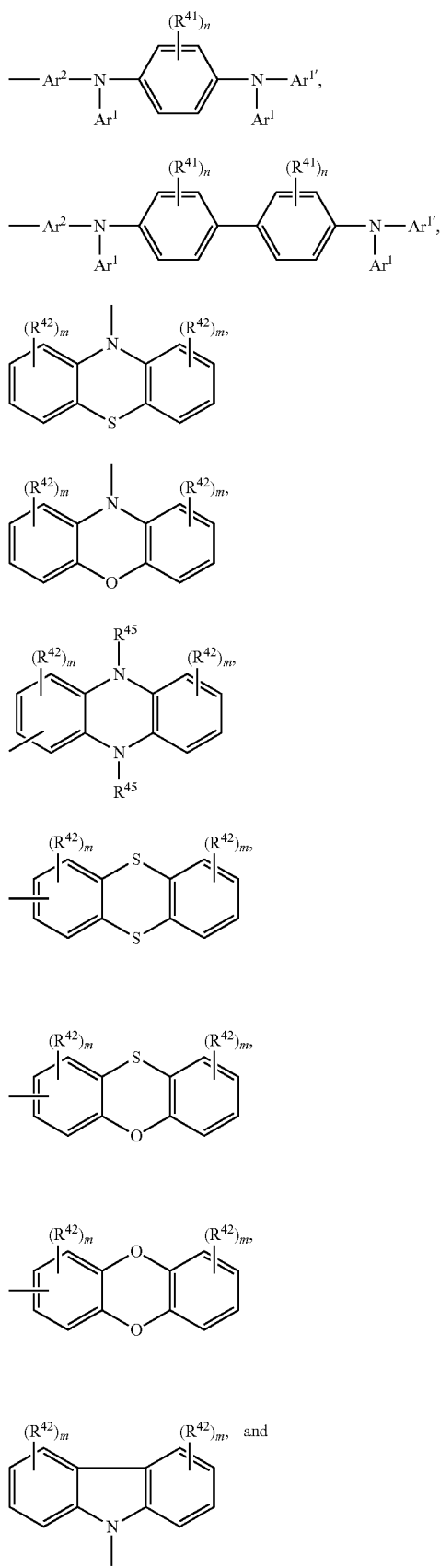

wherein
R⁴¹ can be the same or different at each occurence and is Cl, F, CN, N(R⁴⁵)₂, R₁₀, a C₁-C₂₅alkyl group, a C₄-C₁₈cycloalkyl group, a C₁-C₂₅alkoxy group, in which one or more carbon atoms which are not in neighbourhood to each other could be replaced by —NR⁴⁵—, —O—, —S—, —C(=O)—O—, or —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹, or two or more groups R⁴¹ form a ring system;

R⁴² can be the same or different at each occurence and is CN, a C₁-C₂₅alkyl group, a C₄-C₁₈cycloalkyl group, a C₁-C₂₅alkoxy group, in which one or more carbon atoms which are not in neighbourhood to each other could be replaced by —NR⁴⁵—, —O—, —S—, —C(=O)—O—, or —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹, or two or more groups R⁴¹ form a ring system;

R⁴⁴ can be the same or different at each occurence and are a hydrogen atom, a C₁-C₂₅alkyl group, a C₄-C₁₈cycloalkyl group, a C₁-C₂₅alkoxy group, in which one or more carbon atoms which are not in neighbourhood to each other could be replaced by —NR⁴⁵—, —O—, —S—, —C(=O)—O—, or, —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹, or CN, or two or more groups R⁴⁴, which are in neighbourhood to each other, form a ring;

R⁴⁵ is H, a C₁-C₂₅alkyl group, a C₄-C₁₈cycloalkyl group, a C₁-C₂₅alkoxy group, in which one or more carbon atoms which are not in neighbourhood to each other could be replaced by —NR⁴⁵—, —O—, —S—, —C(=O)—O—, or, —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹;

m can be the same or different at each occurence and is 0, 1, 2, or 3, especially 0, 1, or 2, very especially 0 or 1;

n can be the same or different at each occurence and is 0, 1, 2, or 3, especially 0, 1, or 2, very especially 0 or 1;

Ar¹ and Ar¹' are independently of each other a C₆-C₂₄aryl group, a C₂-C₃₀heteroaryl group, which can be substituted by one or more non-aromatic groups R⁴¹, or NO₂, especially phenyl, naphthyl, anthryl, biphenylyl, 2-fluorenyl, phenanthryl, or perylenyl, which can be substituted by one or more non-aromatic groups R⁴¹, such as
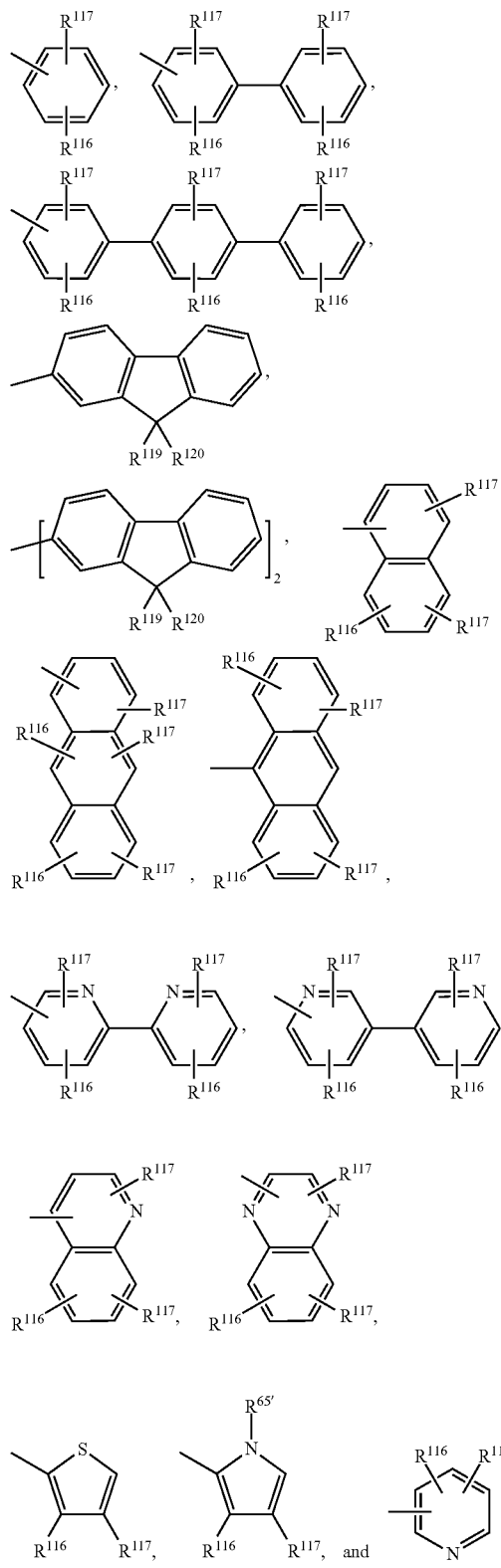
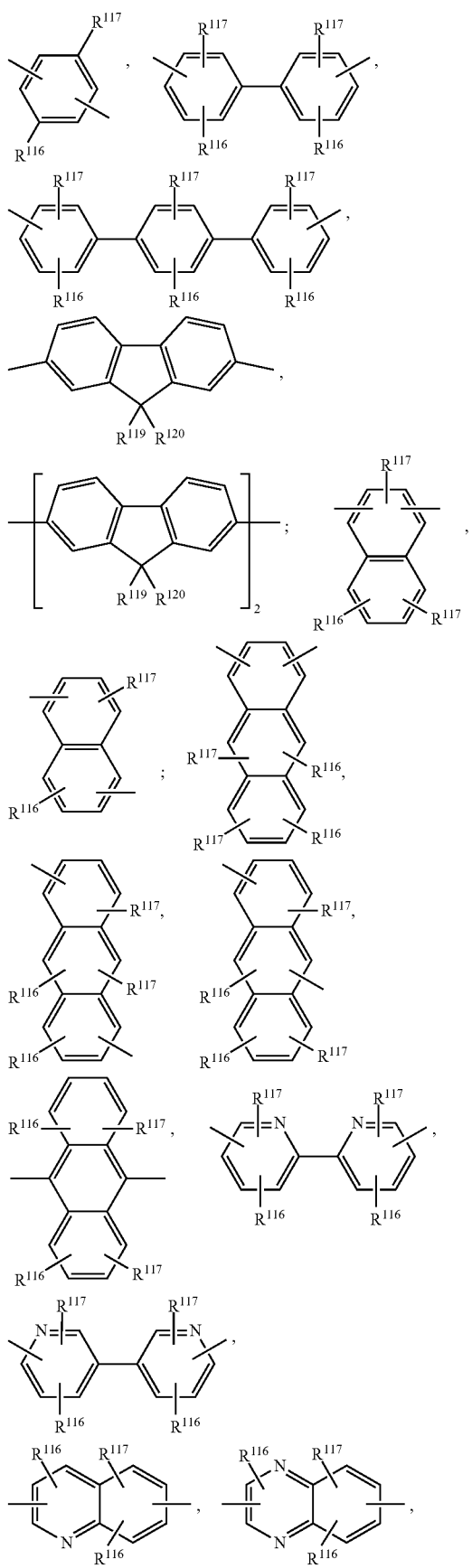
Ar² is a $C_6$-$C_{30}$arylene group, or a $C_2$-$C_{24}$heteroarylene group, which can optionally be substituted, especially

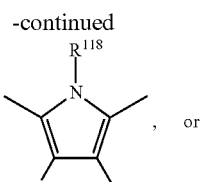, 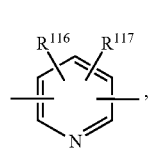, or

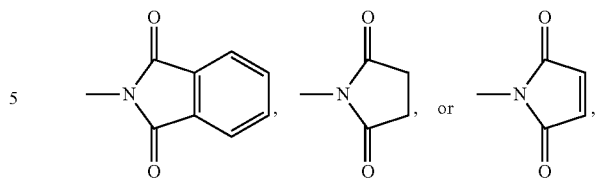

wherein $R^{116}$ and $R^{117}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$;

$R^{119}$ and $R^{120}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $R^{119}$ and $R^{120}$ together form a group of formula =$CR_{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —$SO_2$—, —O—, —N$R^{65}$—, —Si$R^{70}R^{71}$—, —PO$R^{72}$—, —$CR^{63}$=$CR^{64}$—, or —C≡C—, and E is —O$R^{69}$, —S$R^{69}$, —N$R^{65}R^{66}$, —CO$R^{68}$, —COO$R^{67}$, —CON$R^{65}R^{66}$, —CN, or halogen, G is E, or $C_1$-$C_{18}$alkyl, $R^{63}$, $R^{64}$, $R^{65}$ and $R^{66}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, in particular

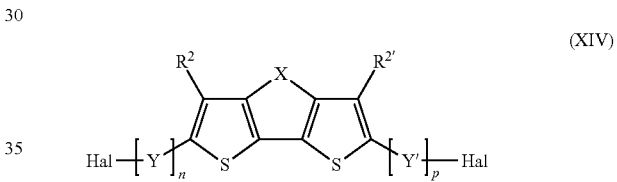, or $R^{67}$ and $R^{68}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is H; $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

The polymerizable aliphatic or aromatic momomer moiety.typically is of the formula PG or is -phenylene-PG, where PG is as defined by the formula PG further above.

A further embodiment of the invention is a polymer obtainable by homopolymerization of a compound of the formula

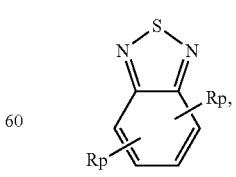 (XIV)

Hal—[Y]$_n$—S—S—[Y']$_p$—Hal wherein Hal stands for halogen, especially Br, and all other symbols are as defined in claims 1-4, or by copolymerization of a compound of the formula XIV with a suitable further monomer such as dihalogenated or diboronated, substituted or unsubstituted $C_1$-$C_{19}$heteroaryls, especially selected from dihalogenated or diboronated mono- or oligothiophenes of the formula Rp—[—S—]$_s$—Rp or benzothiadiazoles of the formula Rp—[benzothiadiazole]—Rp, wherein Rp stands for a residue of a boronic acid or an ester thereof or stands for Hal, and Hal stands for halogen, especially Br, s ranges from 1 to 6, and all other symbols and substituents, if present, are as defined for formula I above.

Preferred are compounds wherein
$R^1$ and $R^{1\prime}$ are independently of each other H, halogen or $SiR^6R^4R^5$;
$R^2$ and $R^{2\prime}$ may be the same or different and are selected from H, $C_1$-$C_{18}$alkyl or $C_5$-$C_{25}$thienylalkyl or phenylalkyl;
R4, R5, R6 independently are selected from $C_1$-$C_{18}$alkyl;
n and p preferably are 0 or 1;
Y, Y' is selected from

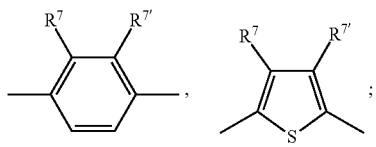

$R^8$ is substituted phenyl or substituted heteroaryl selected from thienyl and dithienyl; or is a moiety of the formula

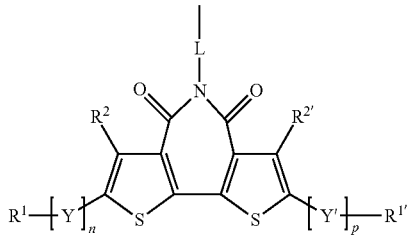
(V)

where $R^1$, $R^{1\prime}$, $R^2$, $R^{2\prime}$, Y, Y', p and n are as defined above and L is as defined.

In case that any neighbouring residues form, together with the carbon atoms they are attached to, a 5-membered unsubstituted or substituted heterocyclic ring comprising at least one hetero atom selected from N, O, S, the structure formed by these residues is often selected from
S—CH=CH; NR—CH=CH; O—CH=CH; S—CH=N; O—CH=N; NR—CH=N; NR—O—NR; NR—S—NR; N—NR—N; N—S—N; N—O—N; NR—N=N; S—N=N; O—N=N;
where each group CH may be unsubstituted or substituted; especially wherein
$R^1$ and $R^{1\prime}$ are independently of each other H, halogen or $SiR^6R^4R^5$;
$R^2$ and $R^{2\prime}$ independently are H or $C_1$-$C_{18}$alkyl;
$R^3$ and $R^{3\prime}$ together form a ring closing structure selected from S—CH=N, O—CH=N, NR—CH=N whose CH moiety is substituted; or are N—S—N; or together form the bridging group

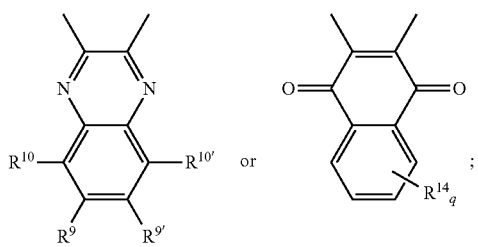

R4, R5, R6 independently are selected from $C_1$-$C_8$alkyl;
n, p are 0;
$R^8$ is substituted phenyl;
$R^9$, $R^{9\prime}$, $R^{10}$ and $R^{10\prime}$ independently are hydrogen and one or more of the neighbouring residues $R^9$ and $R^{9\prime}$ together form a moiety N—CO—N whose nitrogen atoms are substituted; or
neighbouring residues $R^9$ and $R^{9\prime}$ together form a moiety N—CO—N whose nitrogen atoms are substituted; or
$R^9$ and $R^{10}$, and $R^{9\prime}$ and $R^{10\prime}$, each together with the carbon atoms they are attached to, complete an unsubstituted or substituted thienyl ring;
q is 0, 1, 2, 3 or 4, especially 0, and $R^{14}$, if present, is a substituent; and
any substituent, if present, is selected from halogen, $C_1$-$C_{25}$alkyl, SiRR'R", vinyl, allyl, phenyl;
and if bonding to non-aromatic carbon or to sulphur, may also be oxo; and where R, R', R" independently are selected from $C_1$-$C_8$alkyl, phenyl, and R may also be hydrogen; and where each phenyl is unsubstituted or substituted by $C_1$-$C_4$alkyl, $C_1$-$C_4$alkoxy, CHO, vinyl, allyl, allyloxy, acryloyloxy, methacryloyloxy, halogen.

Since $R^3$ and $R^{3\prime}$ both bond to $sp^2$-hybridized carbon, tautomeric forms are possible as well, e.g. where the moiety

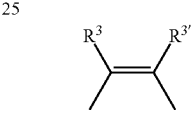

forms the structure

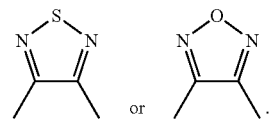

Some compounds of specific interest of the formula I conform to formula II or III:

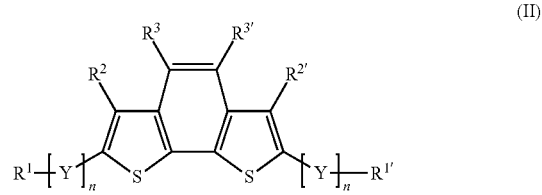
(II)

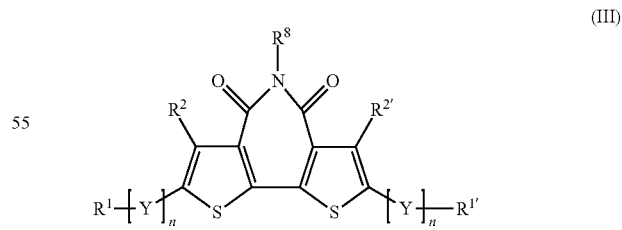
(III)

where all symbols are as defined above for the formula I. More preferred among them are compounds wherein n is 0 or 1, and especially where Y, if present, is a divalent aromatic moiety.

Of special industrial interest are "symmetrical" compounds, i.e. those wherein R1=R1', both Y and indices n are identical, R2=R2', R3=R3' etc.

Further monomers, oligomers or polymers of specific industrial interest are those wherein at least one of $R^2$, $R^{2'}$ or, if present, $R^3$, $R^{3'}$, contain at least 3, especially at least 4 carbon atoms, or wherein $R^3$, $R^{3'}$ together form a cyclic structure such as S—CH=N, O—CH=N, NR—CH=N whose CH moiety is substituted; or are N—S—N; or together form the bridging group

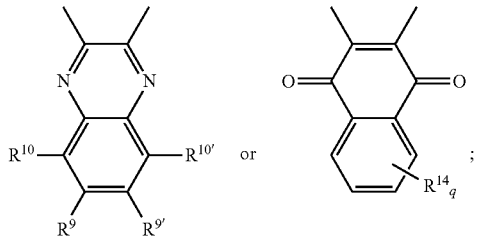

with residues defined as above.

Acyl stands for a residue of a sulfonic acid or especially organic carboxylic acid, which is formed formally by abstraction of the acid OH; examples are formyl, acetyl, propionyl, benzoyl. Generally, $C_1$-$C_{18}$ acyl stands for a radical X'—$R_{11}$, wherein X' is CO or $SO_2$ and $R_{11}$ is selected from monovalent aliphatic or aromatic organic residues, usually from molecular weight up to 300; for example, $R_{11}$ may be selected from $C_1$-$C_{18}$alkyl, $C_2$-$C_{18}$alkenyl, $C_5$-$C_{10}$aryl which may be unsubstituted or substituted by $C_1$-$C_8$alkyl or halogen or $C_1$-$C_8$alkoxy, $C_6$-$C_{16}$arylalkyl which may be unsubstituted or substituted in the aromatic part by $C_1$-$C_8$alkyl or halogen or $C_1$-$C_8$alkoxy, $C_4$-$C_{12}$cycloalkyl, and in case that X' is CO, $R_{11}$ may also be H. Acyl is preferably an aliphatic or aromatic residue of an organic acid —CO—$R_{11}$, usually of 1 to 30 carbon atoms, wherein $R_{11}$ embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

Where aryl (e.g. in $C_4$-$C_{25}$aryl or $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl. The term aryl mainly embraces $C_1$-$C_{18}$aromatic moieties, which may be heterocyclic rings (also denoted as heteroaryl) containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl, especially phenyl. Heteroaryl such as $C_1$-$C_3$heteroaryl or $C_4$-$C_{19}$heteroaryl stands for an aryl group containing at least one heteroatom, especially selected from N, O, S, among the atoms forming the aromatic ring; examples include pyridyl, pyrimidyl, pyridazyl, pyrazyl, thienyl, benzothienyl, dithienyl, pyrryl, furyl, benzofuryl, indyl, carbazolyl, benzotriazolyl, chinolyl, isochinolyl, triazinyl, tetrahydronaphthyl, pyrazolyl, diazolyl, triazolyl, imidazolyl, or a residue of the formula

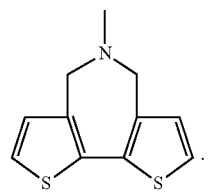

Preferred are $C_4$-$C_{18}$aryl, e.g. selected from phenyl, naphthyl, pyridyl, tetrahydronaphthyl, furyl, thiophenyl, pyrryl, chinolyl, isochinolyl, anthrachinyl, anthracenyl, phenanthryl, pyrenyl, benzothiazolyl, benzoisothiazolyl, benzothienyl, especially $C_6$-$C_{10}$aryl; most preferred is phenyl, naphthyl, furyl, thienyl. Some specific heteroaryl groups in present formula I comprise (usually substituted) dithiophene moieties which classify the compound as a dimer; examples are moieties of the formula

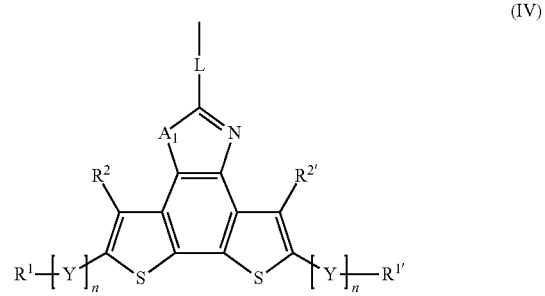

(IV)

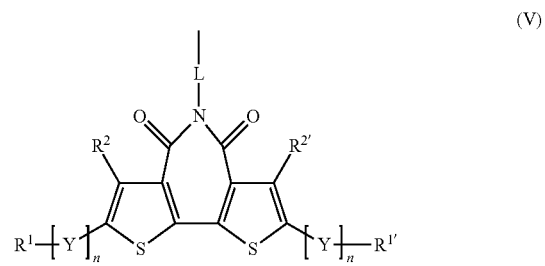

(V)

or $R^3$ and $R^{3'}$ together forming the bridging group

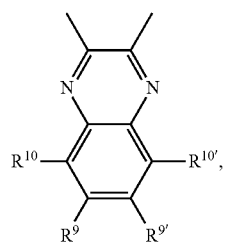

where $R^9$ and $R^{10}$, and $R^{9'}$ and $R^{10'}$, together with the carbon atoms they are attached to, each complete a substituted thienyl ring, to form a moiety of the formula VI:

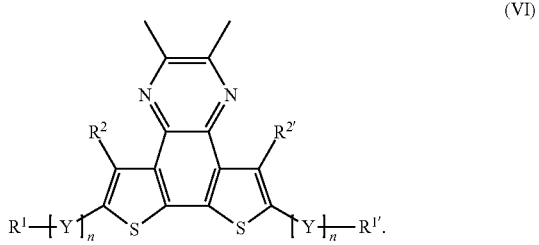

(VI)

In the above formulae IV-VI, all symbols are as defined for formula I; L stands for a divalent organic linking group such as alkylene (e.g. $C_2$-$C_{12}$), phenylene, cycloalkylene; $A_1$ is a divalent moiety O, S, NR.

Halogen denotes I, Br, Cl, F, preferably Cl, Br, especially Br.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH═CH—]$_n$ or —[CH═C(CH$_3$)—]$_n$, where n may be, for example, from the range 2-50. Where not defined otherwise, preferred alkyl contains 1-22 carbon atoms; preferred alkenyl and alkinyl each contains 2-22 carbon atoms, especially 3-22 carbon atoms.

Where indicated as interrupted, any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond of the alkyl or alkylene moiety or a carbon-carbon bond the moiety is bonding to. Hetero-hetero bonds, for example O—O, S—S, NH—NH, etc., usually do not occure; if the interrupted alkyl is additionally substituted, the substituents are generally not α to the heteroatom. If two or more interrupting groups of the type —O—, —NR10-, —S— occur in one radical, they often are identical. Examples for interrupted cycloalkyls are dioxanyl, morpholinyl, piperidinyl, piperazinyl.

The term alkyl, whereever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

Haloalkyl denotes alkyl substituted by halogen; this includes perhalogenated alkyl such as perfluoroalkyl, especially $C_1$-$C_{12}$perfluoroalkyl, which is a branched or unbranched radical such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

Aralkyl is, within the definitions given, usually selected from $C_7$-$C_{24}$aralkyl radicals, preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl.or 3-methyl-5-(1',1',3',3'-tetramethyl-butyl)-benzyl.

The term alkenyl, whereever used, thus mainly embraces uninterrupted and, where appropriate, substituted $C_2$-$C_{22}$alkyl such as vinyl, allyl, etc.

Alkynyl such as $C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic cyclic moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occuring are heterocyclic aliphatic rings (heterocycloalkyl) usually containing 5 to 7 ring members, among them at least 1, especially 1-3, heteromoieties, usually selected from O, S, NR10, where R10 is as explained above for interrupting NR10-groups; examples include $C_4$-$C_{18}$cycloalkyl, which is interrupted by S, O, or NR10, such as piperidyl, tetrahydrofuranyl, piperazinyl and morpholinyl; examples for $C_2$-$C_4$heterocycloalkyl include oxiranyl, oxetanyl, piperazinyl, morpholinyl. Unsaturated variants may be derived from these structures by abstraction of a hydrogen atom on 2 adjacent ring members with formation of a double bond between them; an example for such a moiety is cyclohexenyl.

Alkoxy such as $C_1$-$C_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

Silyl such as SiRR'R" is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with $R_2$ preferably being hydrocarbyl or hydrocarbyloxy. Preferred hydrocarbyl(oxy) are $C_1$-$C_{20}$alkyl(oxy), aryl(oxy) such as phenyl(oxy), $C_1$-$C_9$alkylphenyl(oxy), where "(oxy)" stands for the optional linker "—O—" which may be present or not. More preferred are three $C_1$-$C_{20}$-alkyl or -alkoxy substituents, i.e. substituted silyl then is Si(R12)$_3$ with R12 being $C_1$-$C_{20}$-alkyl or -alkoxy, especially three $C_1$-$C_8$-alkyl substitutents, such as methyl, ethyl, isopropyl, t-butyl or isobutyl.

Cyclic structures formally formed by ring closure, e.g. by interlinking 2 or more adjacent residues to form a bridge often comprise 5 to 12 ring atoms in total. Examples are hydrocarbon rings such as benzene, naphthalene, anthracene, phenanthrene, cycloaliphatic rings such as $C_5$-$C_{12}$cycloalkyl, heteroaryl as explained above in more detail, or heterocyclic rings such as morpholine, piperidine, piperazine, tetrahydrofuran. Where neighbouring groups such as $R^3$ and $R^{3'}$ together, vicinal $R^7$ and $R^{7'}$, neighbouring residues $R^9$ and $R^{9'}$, or $R^9$ and $R^{10}$ and/or $R^{9'}$ and $R^{10'}$, together with the carbon atoms they are attached to, complete a 5-membered unsubstituted or substituted heterocyclic ring comprising at least one hetero atom selected from N, O, S, the resulting structures often are from the formulae

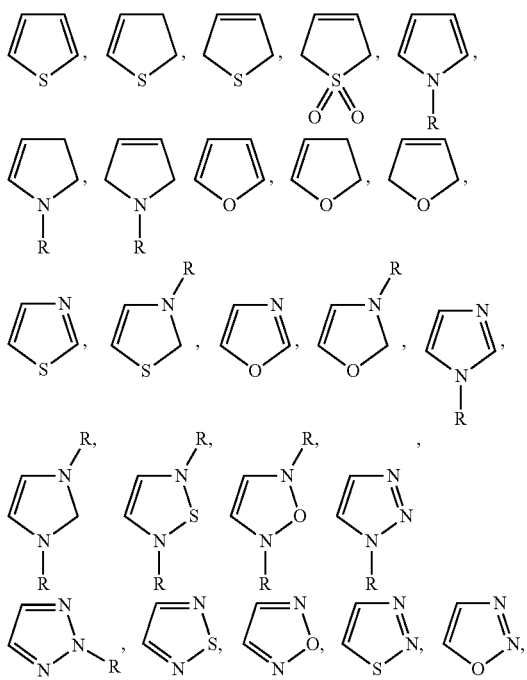

which are unsubstituted or substituted by R as indicated, or by another substituent whereelse possible, with vicinal sp2-hybridized carbon atoms bonding to the remaining structure. Unsaturated rings among them, i.e. those containing the maximum possible number of double bonds, are preferred.

A key step in the preparation of dimetic thiophene educts for the preparation of the present compounds relates to reactions of the intermediate 3,3'-dilithio-2,2'-dithiophene

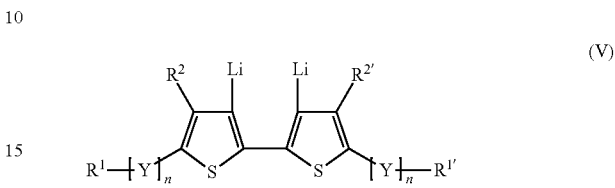

(V)

wherein the residues are as defined further above; especially preferred is the one with n=0. This intermediate is usually formed in situ, and reacted further to form the desired 3,3'-disubstituted dithiophenes, according to the following scheme:

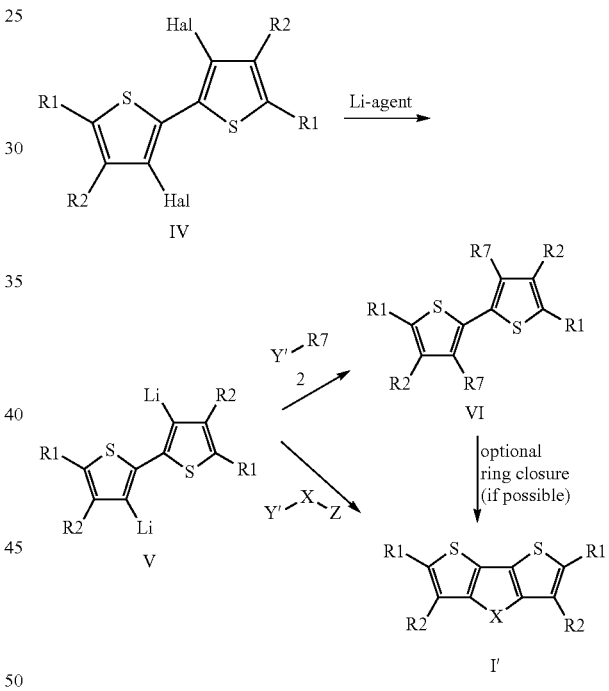

wherein Hal stands for halogen, especially Br, further residues are as defined above, where identically named residues such as R1 may be identical or different (see pending appl. No. PCT/EP2009/052646). R1 is usually different from hydrogen and preferably halogen (such as Br) or silyl (e.g. SiR4R5R6 as defined above). Y' and Z are advantageously selected from moieties able to form a covalent bond with thienyl-lithium, examples for suitable reagents Y'-R7 and Y'—X—Z are DMF, $CO_2$, esters, amides, acylchlorides, carbamoylchlorides, chlorosilanes, boronates etc. The lithiating agent may be a Li-alkyl such as butyllithium. The reactions are usually carried out in analogy to lithium reactions known in the art, e.g. under exclusion of oxygen (e.g. using $N_2$, Ar), at low temperature (e.g. −100 to 0° C.), using a suitable solvent such as ethers (diethylether, THF, dioxane etc.) or hydrocarbons (e.g. $C_5$-$C_8$alkanes).

Reactive bridging groups X for further conversion to the present compounds of the formula I are, for example, X as —CO—CO— (obtainable e.g. via ring-closure reaction with 1,4-dimethylpiperazine-2,3-dione, see present examples 18 and 21) or as —CO—NR—CO— (obtainable e.g. via ring-closure reaction using $CO_2$/acetic anhydride, followed by amination; see present example 10).

The compounds according to the invention are useful as semiconductors and have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics (solar cells) and photodiodes. The invention thus further pertains to a semiconductor device, comprising a compound according to any of claims 1-9, especially a diode, a photodiode, an organic photovoltaic (PV) device (solar cell), an organic field effect transistor, or a device containing a diode and/or a photodiode and/or an organic field effect transistor, and/or a solar cell; especially containing the compound of the formula I, and/or an oligomer or polymer according to the invention, as a layer having a thickness from the range 5 to 1000 nm, on a rigid or flexible solid substrate, as well as to an organic semiconductor material, layer or component, comprising a compound of the formula I, and/or an oligomer or polymer according to the invention.

The invention further includes a process for the preparation of an organic semiconductor device, which process comprises applying a solution and/or dispersion of a compound of the formula I, and/or an oligomer or polymer according to the invention, in an organic solvent to a suitable substrate and removing the solvent.

The invention thus includes the use of a compound of the formula I, and/or an oligomer or polymer as described above, as a charge-transport material, semiconducting material, electrically conducting material, photoconducting material, light emitting material, surface-modifying material, electrode material in a battery, alignment layer, or in an organic field effect transistor, integrated circuit, thin film transistor, display, RFID tag, electro- or photoluminescent device, backlight of a display, photovoltaic or sensor device, charge injection layer, photodiode, Schottky diode, memory device (e.g. FeFET), planarising layer, antistatics, conductive substrate or pattern, photoconductor, or electrophotographic application or recording material.

As noted above, the compounds of the invention according to the present invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals, metal oxides, such as, for example, indium tin oxide (ITO), and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, $2^{nd}$ edition, John Wiley and Sons, page 492, New York (1981)). These components can be assembled in a variety of configurations. More specifically, an OFET has an organic semiconductor layer.

Typically, a substrate supports the OFET during manufacturing, testing, and/or use. Optionally, the substrate can provide an electrical function for the OFET. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide, or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OFETs, the same material can provide the gate electrode function and also provide the support function of the substrate. For example, doped silicon can function as the gate electrode and support the OFET.

The gate dielectric is generally provided on the gate electrode. This gate dielectric electrically insulates the gate electrode from the balance of the OFET device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly(vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem.

Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybride materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting monomers or polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides an organic field effect transistor device comprising
a plurality of electrically conducting gate electrodes disposed on a substrate;
a gate insulator layer disposed on said electrically conducting gate electrodes;
a plurality of sets of electrically conductive source and drain electrodes disposed on said insulator layer such that each of said sets is in alignment with each of said gate electrodes;
an organic semiconductor layer disposed in the channel between source and drain electrodes on said insulator layer substantially overlapping said gate electrodes; wherein said organic semiconductor layer comprises a compound of the present invention, or an organic semiconductor material, layer or component.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer of a compound of the present invention on said insulator layer such that said layer of the compound of the present invention, or a mixture containing a compound of the present invention, substantially overlaps said gate electrodes; thereby producing the thin film transistor device.

Alternatively, an OFET is fabricated by, for example, by solution deposition of a small molecule or a polymer on a highly doped silicon substrate covered with a thermally grown oxide layer followed by vacuum deposition and patterning of source and drain electrodes.

In yet another approach, an OFET is fabricated by deposition of source and drain electrodes on a highly doped silicon substrate covered with a thermally grown oxide and then solution deposition of the compound to form a thin film.

The gate electrode could also be a patterned metal gate electrode on a substrate or a conducting material such as, a conducting polymer, which is then coated with an insulator applied either by solution coating or by vacuum deposition on the patterned gate electrodes.

Any suitable solvent can be used to dissolve, and/or disperse the compounds of the present application, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, decaline, anisole, xylene, ethyl acetate, methyl ethyl ketone, dimethyl formamide, chloroform, chlorobenzene, dichlorobenzene, trichlorobenzene, propylene glycol monomethyl ether acetate (PGMEA) and mixtures thereof. Preferred solvents are xylene, toluene, tetraline, decaline, chlorinated ones such as chloroform, chlorobenzene, ortho-dichlorobenzene, trichlorobenzene and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising the semiconductor material of the present invention, which is not fully dissolved in a solvent. The dispersion can be done selecting a composition including at least a compound of the present invention, or a mixture containing a compound of the present invention, and a solvent, wherein the compound exhibits lower solubility in the solvent at room temperature but exhibits greater solubility in the solvent at an elevated temperature, wherein the composition gels when the elevated temperature is lowered to a first lower temperature without agitation;
dissolving at the elevated temperature at least a portion of the compound in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of the present invention, or a mixture containing a compound of the present invention. The degree of solubility of the compound of the present invention in the solvent may vary for example from 0% to about 20% solubility, particularly from 0% to about 5% solubility.

Preferably, the thickness of the organic semiconductor layer is in the range of from about 5 to about 1000 nm, especially the thickness is in the range of from about 10 to about 100 nm.

The compounds of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambipolarity the material can also be used in Organic Light Emitting Transistors (OLET). Especially suitable for light emitting devices (OLED or OLET) are copolymers of the invention comprising one or more luminiscent (especially phosphorescent) comonomers (e.g. of formula (1) or (2) described further above).

A further aspect of the present invention is an organic semiconductor material, layer or component comprising one or more compounds of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The compounds of the present invention are typically used as organic semiconductors in form of thin organic layers or films, preferably less than 30 microns thick. Typically the semiconducting layer of the present invention is at most 1 micron (=1 µm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
  a source electrode,
  a drain electrode,
  a gate electrode,
  a semiconducting layer,
  one or more gate insulator layers, and
  optionally a substrate, wherein the semiconductor layer comprises one or more compounds of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of the present invention located on the second side of the insulator, and a drain electrode and a source electrode located on the compound layer.

The OFET device can be a top gate device or a bottom gate device.

Suitable structures and manufacturing methods of an OFET device are known to the skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a compound of the present invention may additionally comprise at least another material. The other material can be, but is not restricted to another compound of the present invention, a semi-conducting polymer, a polymeric binder, organic small molecules different from a compound of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more compounds of the present invention and a polymeric binder. The ratio of the compounds of the present invention to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The compounds of the present invention are advantageously used in organic photovoltaic (PV) devices (solar cells). Accordingly, the invention provides PV devices comprising a compound according to the present invention. A device of this construction will also have rectifying properties so may also be termed a photodiode. Photoresponsive devices have application as solar cells which generate electricity from light and as photodetectors which measure or detect light.

The PV device comprise in this order:
(a) a cathode (electrode),
(b) optionally a transition layer, such as an alkali halogenide, especially lithium fluoride,
(c) a photoactive layer, (d) optionally a smoothing layer,
(e) an anode (electrode),
(f) a substrate.

The photoactive layer comprises the compounds of the present invention. Preferably, the photoactive layer is made of a conjugated compound of the present invention, as an electron donor and an acceptor material, like a fullerene, particularly a functionalized fullerene PCBM, as an electron acceptor. For heterojunction solar cells the active layer comprises preferably a mixture of a compound of the present invention and a fullerene, such as [60]PCBM (=6,6-phenyl-$C_{61}$-butyric acid methyl ester), or [70]PCBM, in a weight ratio of 1:1 to 1:3.

The following examples are included for illustrative purposes only and do not limit the scope of the claims. Unless otherwise stated, all parts and percentages are by weight.

Weight-average molecular weight (Mw) and polydispersity (Mw/Mn=PD) are determined by High Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgeI Olexis" column from Polymer Laboratories (Church Stretton, UK); with an average particle size of 13 µm (dimensions 300×8 mm I.D.) Mobile phase: 1,2,4-trichlorobenzene purified by vacuum distillation and stabilised by butylhydroxytoluene (BHT, 200 mg/l), Chromatographic temperature: 150° C.; Mobile phase flow: 1 ml/min; Solute concentration: about 1 mg/ml; Injection volume: 200 µl; Detection: RI, Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i. e., PS 1'930'000, PS 1'460'000, PS 1'075'000, PS 560'000, PS 330'000, PS 96'000, PS 52'000, PS 30'300, PS 10'100, PS 5'050 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

The following examples are included for illustrative purposes only and are not to be construed to limit the scope of the claims. Unless otherwise stated, all parts and percentages are by weight. Room temperature denotes a temperature range 18-23° C.; similarly ambient conditions, which also imply atmospheric pressure. Abbreviations:
NBS N-bromosuccinimide
LDA Lithium diisopropylamide
THF tetrahydrofuran
TBME tert-butyl methylether
AIBN 2,2'-azobisisobutyronitrile
Mw molecular weight (weight average)
PDI polydispersity

EXAMPLE 1

General Procedure for Suzuki Polymerization

The starting material comprises a suitable α,ω-di(bromoaryl) monomer (1). In a three neck-flask, 0.71 g of potassium phosphate ($K_3PO_4$) dissolved in 2.1 ml of water (previously degassed with argon) is added to a degassed solution of 1.00 g of 1, an equivalent amount of the second monomer in form of a suitable α,ω-diboronic acid bis(1,3-propanediol)ester, 16.0 mg of tri-tert-butylphosphonium tetrafluoroborate (($t$-Bu$)_3$P*HBF$_4$) and 26.0 mg of tris(dibenzylideneacetone) dipalladium (0) ($Pd_2(dba)_3$) in 10 ml of tetrahydrofuran. The reaction mixture is heated to 50° C. for approximately 13 hours. Subsequently, 18 mg bromo-thiophene and 20 minutes later 23 mg thiophene-boronic acid pinacol ester are added to stop the polymerisation reaction. The reaction mixture is cooled to room temperature and precipitated in methanol. The residue is purified by soxhlet extraction using pentane and the polymer is then extracted with cyclohexane and dried.

EXAMPLE 10

Synthesis of Building Block 17

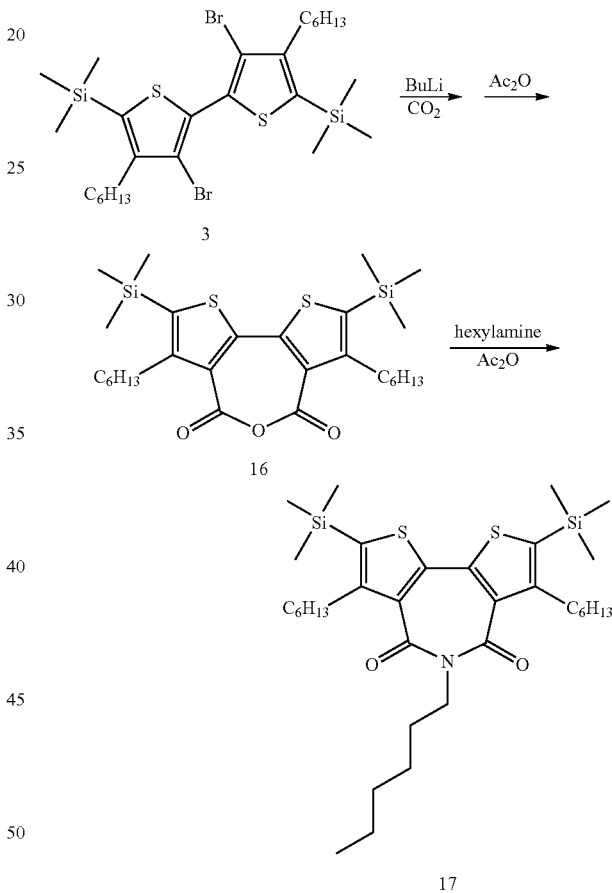

a) 10 g 3 (obtained in analogy to example 11a below) are lithiated as described in Ex.11c (below) and then cooled to −78° C. 5 g solid carbon dioxide is added in one portion and the solution is allowed to warm to room temperature. The solution is again cooled to 0° C., quenched with diluted HCl and twice extracted with TBME. The combined organic phases are washed with brine, dried over sodium sulphate and evaporated to dryness. 50 ml acetic anhydride is added to the residue and the suspension is refluxed for 2 hours. After cooling down the slurry is extracted several times with hexane, the combined hexane phases are evaporated to dryness and further dried in a vacuum oven affording 7.4 g 16 as a reddish-white solid.

b) The product from above is dissolved in THF, treated at 0° C. with 2.2 eq. hexylamine and stirred for 1 hour at room temperature. After standard work-up (TBME, diluted HCl, brine) the residue is suspended in acetic acid, treated with 10 eq. each of acetic anhydride and sodium acetate and refluxed for 16 hours. Then most of the solvent is evaporated and the residue is suspended in aqueous sodium bicarbonate, followed by extraction with TBME. The combined organic layers are washed with brine, dried and evaporated dryness affording 7.6 g 17 as a yellowish solid.

EXAMPLE 11

Synthesis of Building Block 26

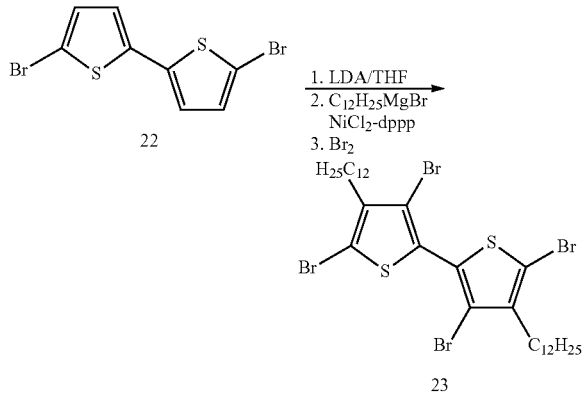

a) A solution of 40 g of 22 in 200 ml of dry tetrahydrofuran (THF) is added rapidly to a solution of lithium diisopropylamide (LDA, prepared from 100 ml of 2.7 M solution of butyllithium in hexane and 28.8 g diisopropylamine in 200 ml of dry THF) at −70° C. under nitrogen atmosphere. After the colour of the mixture has become orange-brown, the mixture is allowed to warm to −20° C. and then 100 ml of water are added. The organic phase is separated, washed with brine, dried and evaporated. The residue is recrystallized from methanol to obtain 36.5 g of 4,4'-dibromo-2,2'-dithiophene as an off-white powder (yield: 91.2%).

A solution of n-dodecyl magnesium bromide in ether (prepared from 9 g of magnesium turnings and 87.0 g n-dodecylbromide in 200 ml of diethylether) is slowly added to a solution of 40 g of 4,4'-dibromo-2,2'-dithiophene. 1 mol % $NiCl_2(dppp)$ ($dppp=Ph_2PCH_2Ch_2CH_2PPh_2$) in 200 ml of diethylether is added in such a way, that the internal temperature does not exceed 20° C. Then the mixture is stirred at room temperature for 2 hours and 200 ml of water are added thereto. The organic phase is separated, washed with diluted hydrochloric acid and brine, dried and evaporated. The residue is suspended in methanol and 55.8 g of 4,4'-n-didodecyl-2,2-dithiophene is obtained as a beige powder by filtation (yield: 70%). 12.8 g of bromine are added dropwise to a solution of 10.1 g 4,4'-n-didodecyl-2,2-dithiophene in 100 ml chloroform and 40 ml acetic acid at 0° C. under nitrogen atmosphere. The mixture is heated at 60° C. for 16 hours. After cooling to room temperature the mixture is treated with 50 ml of a saturated solution of sodium sulfite. The organic phase is separated, washed with a saturated aqueous solution of sodium hydrogen carbonate and brine, dried and evaporated. The residue is suspended in methanol and 14.5 g of 23 is obtained as a beige powder by filtration. $^1$H-NMR: δ (ppm) 0.89 (t, 6H), 1.27 (m, 36 H (18×CH$_2$)), 1.56 (m, 4H), 2.67 (dd, 4H); $^{13}$C-NMR: δ (ppm) 14.51 (CH$_3$), 23.08 (CH$_2$), 28.93-32.31 (9×CH$_2$), 111.28 (C5), 114.82 (C3), 128.80 (C4), 141.68 (C2)

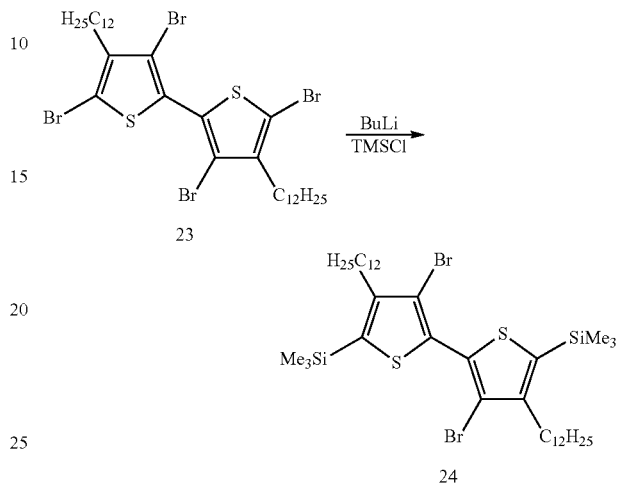

b) 10 g of 23 are dissolved in 150 ml dry THF and 70 ml heptane under nitrogen atmosphere and the solution is cooled to −20° C. After adding of 9.5 ml of a 2.7 M solution of butyllithium in heptane the obtained solution is stirred at −20° C. for 1 hour, 3 ml of trimethylsilyl chloride (TMSCI) is added thereto, the resulting mixture is stirred at −20° for 15 minutes and then allowed to warm to room temperature. After stirring for an additional hour 50 ml of water are added. The organic phase is separated, washed with brine, dried and evaporated to obtain 9.9 g of 24 as an orange-brown semisolid residue (yield: 100%).

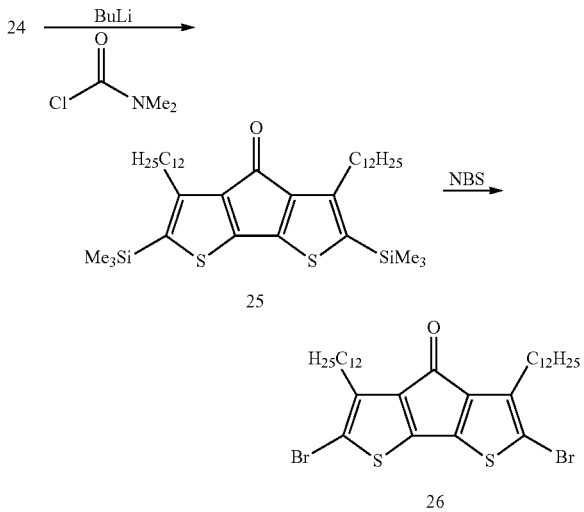

c) Intermediate 24 is dissolved in 500 ml of dry THF under nitrogen atmosphere and the solution is cooled to −60° C. A 2.7 M solution of BuLi in heptane are added at once and the mixture is allowed to warm to −30° C. followed by addition of 11.5 ml dimethylcarbamyl chloride. After stirring at −20° C. for 15 minutes the mixture is allowed to warm to 0° C. and 100 ml of water are added thereto. The organic phase is separated, washed with brine, dried and evaporated to obtain 25 as a red residue (yield: 58%). $^1$H-NMR: δ (ppm) 0.35 (s, 18 H), 0.90 (t, 6H), 1.28 (m, 36 H (18×CH2)), 1.61 (m, 4H), 2.69 (dd, 4H); $^{13}$C-NMR: δ (ppm) 0.00 (TMS), 13.72 (CH$_3$), 22.23 (CH2), 28.95-31.52 (9×CH$_2$), 136.45, 142.98, 146.82, 152.40, 183.66 d) For the further reaction to 26, it is not necessary to isolate 25. The organic phase of c) is separated and washed with brine. 37.4 g of N-bromosuccinimide (NBS) are added thereto at 0° C., the mixture is stirred at 0° C. for 30 minutes and at room temperature for an additional hour. After evaporation the residue is washed with water and suspended in 200 ml of methanol. The mixture is heated under reflux for 1 hour and after cooling to room temperature. The product 26 is obtained as dark-violett flakes by filtation (yield: 55%). $^1$H-NMR: δ (ppm) 0.88 (t, 6H), 1.26 (m, 36 H (18×CH$_2$)), 1.59 (m, 4H), 2.57 (dd, 4H) $^{13}$C-NMR: δ (ppm) 14.50 (CH$_3$), 23.09 (CH$_2$), 29.40-32.31 (9×CH$_2$), 111.10 (C—Br), 137.31, 139.78, 147.35, 182.13.

EXAMPLE 12

Synthesis of Building Block 27

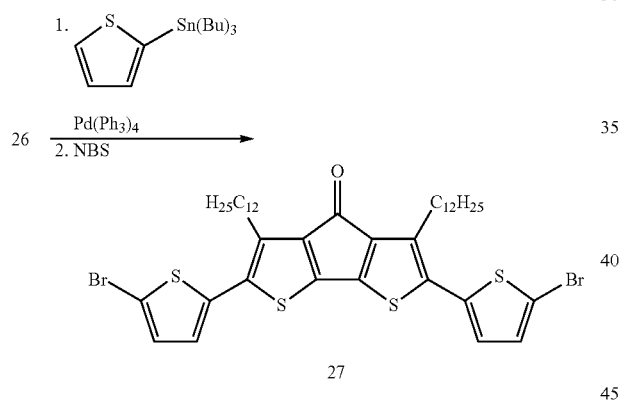

0.94 g of tetrakistriphenylphosphino palladium are added to a degassed solution of 11.13 g of 26 and 15.1 g of 2-(tributyltin)-thiophene in 100 ml of toluene and the mixture is heated under reflux for 16 h, cooled to room temperature and filtered through silica gel. The filtrate is evaporated, the residue is suspended in 100 ml of methanol, stirred for 1 hour and 10.5 g of the 3,5-didodecyl-2,6-di(thien-2-yl)-cyclopenta[2,1-b;3,4-b']dithiophen-4-one are obtained as dark-bluish solid by filtration (yield: 95%). $^1$H-NMR: δ (ppm) 0.93 (t, 6H), 1.32 (m, 36 H (18×CH$_2$)), 1.65 (m, 4H), 2.83 (dd, 4H), 7.06 (m, 2H), 7.10 (m. 2H), 7.32 (dd, 2H). $^{13}$C-NMR: δ (ppm) 14.51 (CH$_3$), 23.08 (CH2), 28.60-32.31 (9×CH$_2$), 126.02, 126.32, 127.68, 134.15, 135.32, 141.04, 146.84, 184.20 (C=O)

11.15 g of the preceding product are dissolved in 100 ml of THF and the solution is cooled to 0° C. 5.7 g NBS are added thereto, and the resulting mixture is stirred at 0° C. for 30 minutes and at room temperature for an additional hour. The solvent is evaporated, the residue is suspended in methanol and 13.0 g of 27 are obtained as dark-bluish solid by filtration (yield: 95%).

EXAMPLE 13

Synthesis of Building Block 28

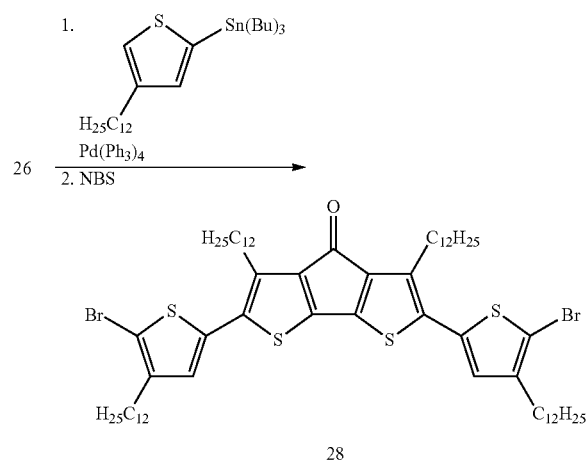

Using 4-dodecyl-2-(tributyltin)-thiophene, the corresponding dialkylated variants 28 are obtained in an analogous procedure. $^1$H-NMR: δ (ppm) 0.85 (2×t, 12H), 1.1-1.4 (m, 40 H), 1.59 (m, 8H), 2.48 (dd, 8H), 7.77 (s, 2H)

EXAMPLE 14

Synthesis of Building Block 30

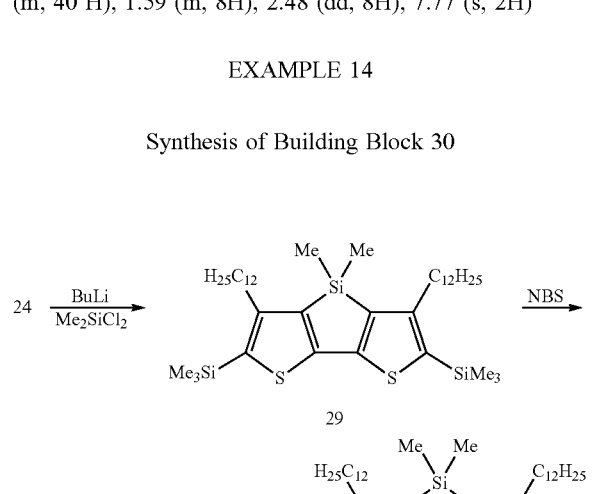

a) A solution of 24 in 150 ml of dry THF is cooled to −40° C. 16 ml of a 2.7 M solution of BuLi in heptane are added and the resulting solution is stirred at −20° C. for 15 minutes. 2.58 g of dimethyl dichloro silane are added thereto and the mixture is stirred at 0° C. for 30 minutes and at room temperature for an additional hour followed by adding of 50 ml of 1 N hydrochloric acid. The organic phase is separated, washed with brine, dried and evaporated to obtain 29 as colourless liquid (yield: 95%).

b) Bromination using NBS in analogy to the method shown in example 11d yields 30.

EXAMPLE 15

Synthesis of Building Block 31

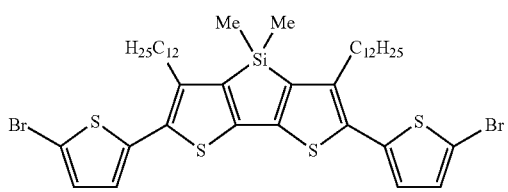

31

The same reaction sequence shown in example 12, but using the starting material 30 yielding in 31:

$^{1}$H-NMR: δ (ppm) 0.40 (s, 6H), 0.78 (t, 6H), 1.1-1.3 (m, 36H), 1.45 (m, 4H), 2.61 (dd, 4H), 6.73 (d, 2H), 6.87 (d, 2H) $^{13}$C-NMR: δ (ppm) 0.00, 17.20, 25.77, 31-38 (tot. 20 C), 114.40, 127.95, 133.05, 133.50, 140.71, 147.83, 148.19, 149.58

EXAMPLE 16

Synthesis of Building Block 32

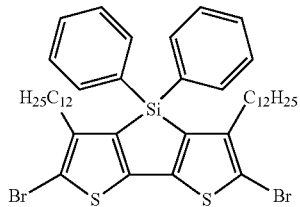

32

The same reaction sequence shown in example 14, but replacing dimethyl dichloro silane with the equivalent amount of diphenyl dichloro silane, gives 32 in 90% overall yield. $^{13}$C-NMR: δ (ppm) 0.02, 17.30, 25.89, 31-38 (tot. 20 C), 111.186, 144.48, 147.95, 150.01

EXAMPLE 17

Synthesis of Building Block 33

33

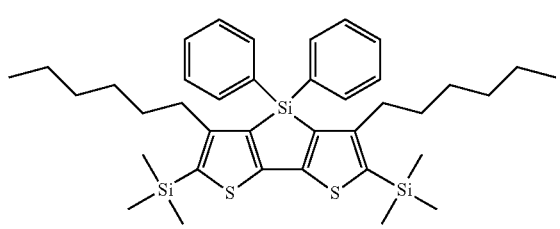

In an analogous process (example 14 and 16), compound 33 can be synthesized.

$^{1}$H-NMR: δ (ppm) 0.34 (s, 18 H), 0.87 (t, 6H), 1.1-1.4 (m, 16H), 2.41 (dd, 4H), 7.3-7.4 (m, 8H), 7.65 (m, 2H). $^{13}$C-NMR: δ (ppm) 0.00, 14.72, 23.15, 28.72, 29.31, 29.89, 31.56, 129.84, 135.02, 136.01, 141.08, 141.41, 155.18

EXAMPLE 18

Synthesis of Building Block 35

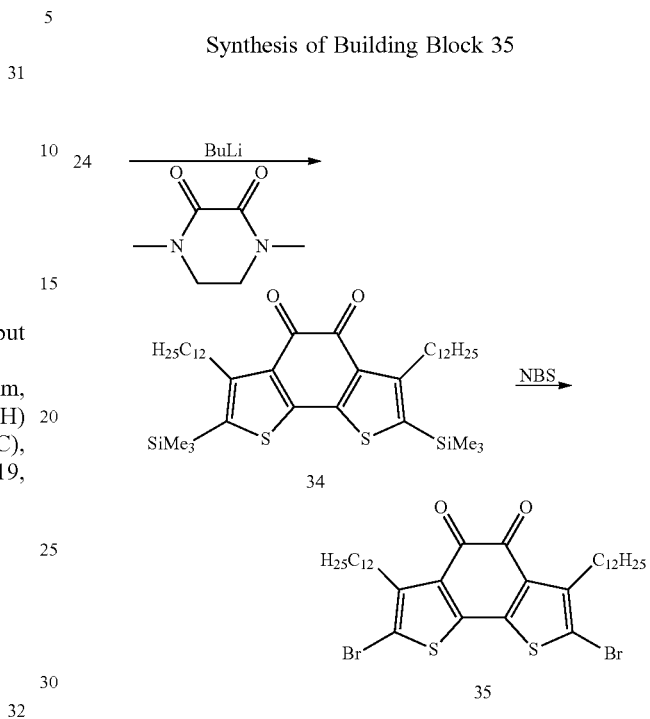

a) 34 is obtained as red powder (yield: 40%) according to example 12 with the exception that 3.20 g of 1,4-dimethylpiperazine-2,3-dione are used instead of dichlorodimethylsilane.

$^{1}$H-NMR: δ (ppm) 0.00 (s, 18H), 0.87 (t, 6H), 1.24 (m, 36 H (18×CH$_2$)), 1.62 (m, 4H), 2.57 (dd, 4H). $^{13}$C-NMR: δ (ppm) 0.00 (TMS), 13.79 (CH$_3$), 21.97 (CH2), 28.63-31.72 (10×CH$_2$), 136.45, 142.98, 146.82, 152.40, 174.83 b) Bromination using NBS in analogy to the method shown in example 11d yields 35.

EXAMPLE 19

Synthesis of Building Block 39

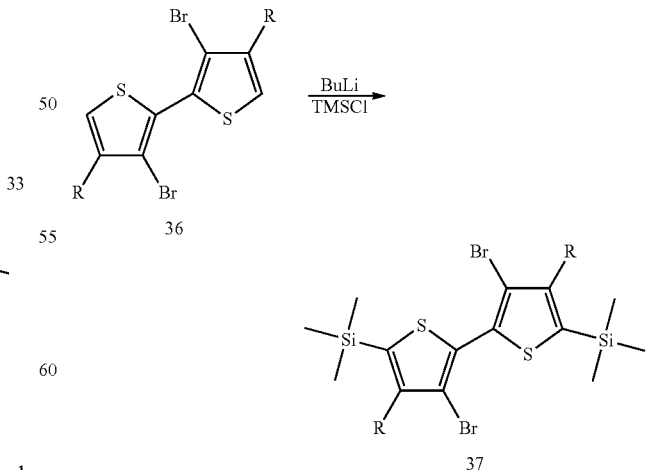

(R = H)

a) To a freshly prepared LDA solution (82 ml butyllithium [2.7 m in heptane], 22.6 g di-isopropyl amine and 300 ml dry THF) at −78° C. under a nitrogen atmosphere, a solution of 32.4 g 3,3'-dibromo-2,2'-dithiophene 36 in 150 ml of dry THF is slowly added. The solution is slowly warmed to −20° C., stirred for 15 minutes and then re-cooled to −78° C. 27.2 g trimethyl silylchloride is added at once and the solution is slowly allowed to warm to 0° C. After stirring for 1 hour at 0° C. the reaction mixture is quenched by adding 100 ml water. The phases are separated and the organic phase is washed twice with brine and dried over sodium sulphate. The residue is suspended in methanol and the formed solid is recovered by filtration and dried under vacuum. Affords 43 g (92%) of the title compound 37 as an off-white powder.

$^1$H-NMR: δ (ppm) 0.00 (s, 18 H), 6.81 (s, 2 H); $^{13}$C-NMR: δ (ppm) 0.00 (TMS), 113.14 (C3), 134.11, 137.15, 143.05

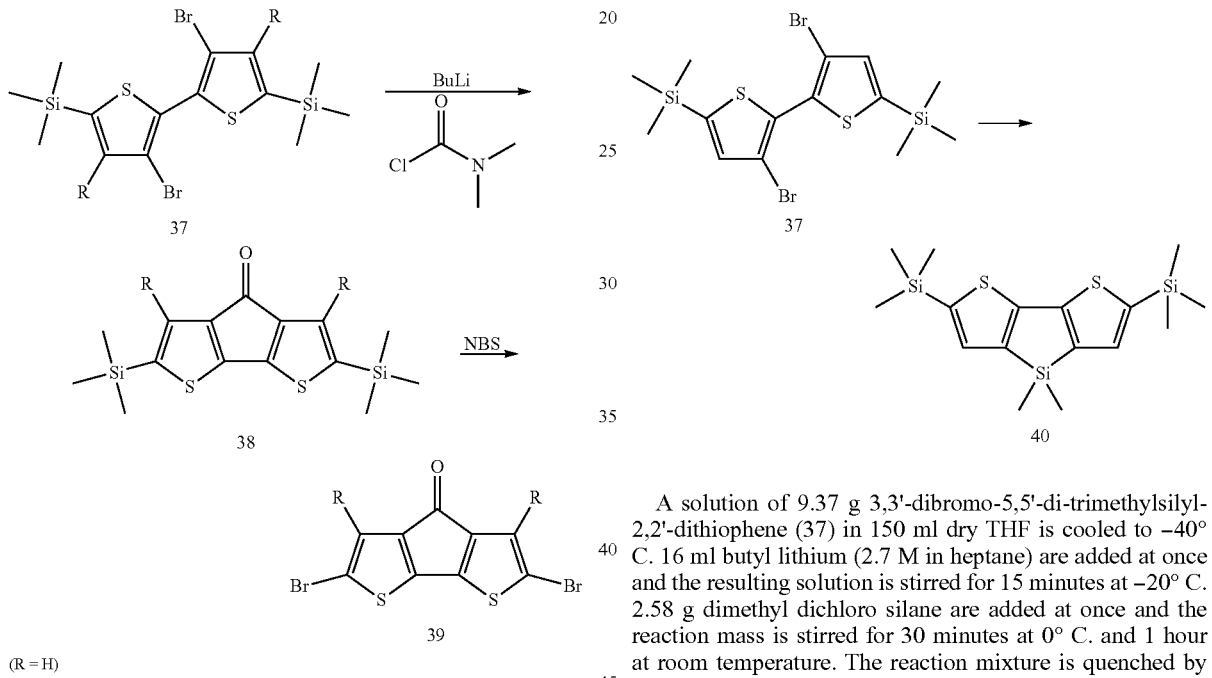

(R = H)

b) 46.8 g 3,3'-dibromo-5,5'-di-trimethylsilyl-2,2'-dithiophene 37 is dissolved in 500 ml of dry THF under a nitrogen atmosphere and cooled to −60° C. 78 ml butyl lithium (2.7 M in heptane) is added at once. The temperature rises to approximately −40° C. The dry ice bath is removed and the reaction mixture is slowly warmed to −30° C. At this point 11.5 ml dimethyl carbamoylchloride in 20 ml dry THF is added at once. The temperature rises to approximately −20° C. and the reaction mixture is stirred at that temperature for 15 minutes and then slowly warmed to 0° C. The reaction mixture is quenched by adding 100 ml water. The phases are separated and the organic phase is washed twice with brine and dried over sodium sulphate. Evaporation of the solvent affords 33.1 g of a red residue, which contains approximately 90% product 38 (NMR; corresponds to 88.5% yield). Purification can be achieved either by flash chromatography or suspension in methanol.

$^1$H-NMR: δ (ppm) 7.05 (s, 2H); $^{13}$C-NMR: δ (ppm) 125.41 (C4), 141.08 (C2), 147.42 (C3), 152.21 (C5), 180.51 (C=O)

c) The organic phase from reaction step b) can be directly used for the bromination step by adding 37.4 g N-bromo succinimide are added to the organic phase at once at 0° C. The reaction mixture is stirred for 30 minutes at 0° C. and 1 hour at room temperature. After evaporation to dryness the residue is washed twice with 200 ml water each, which is decanted, and then boiled for 1 hour in 200 ml methanol. After cooling to room temperature the product is collected by filtration. Affords 30.1 g (85.2%) of the title compound 39 as dark-violet flakes. $^1$H-NMR: δ (ppm) 6.99 (s, 2H); $^{13}$C-NMR: δ (ppm) 114.17 (C5), 124.62 (C4), 139.74 (C2), 148.80 (C3), 180.51 (C=O)

EXAMPLE 20

Synthesis of Building Block 40

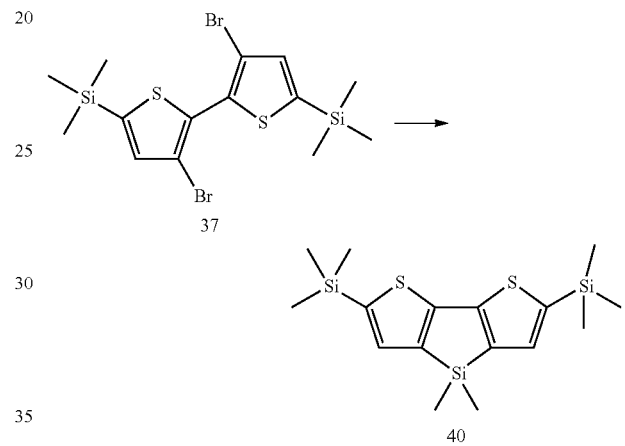

A solution of 9.37 g 3,3'-dibromo-5,5'-di-trimethylsilyl-2,2'-dithiophene (37) in 150 ml dry THF is cooled to −40° C. 16 ml butyl lithium (2.7 M in heptane) are added at once and the resulting solution is stirred for 15 minutes at −20° C. 2.58 g dimethyl dichloro silane are added at once and the reaction mass is stirred for 30 minutes at 0° C. and 1 hour at room temperature. The reaction mixture is quenched by adding 50 ml 1 N HCl. The phases are separated and the organic phase is washed twice with brine and dried over sodium sulphate. Evaporation of the solvent affords 6.95 g (95% of th.) of the title compound 40 as colourless liquid, which is almost pure as determined by NMR. $^1$H-NMR: δ (ppm) 0.00 (s, 18H), 0.08 (s, 6H), 6.83 (s, 2 H)

EXAMPLE 21

Synthesis of Building Blocks 42-46

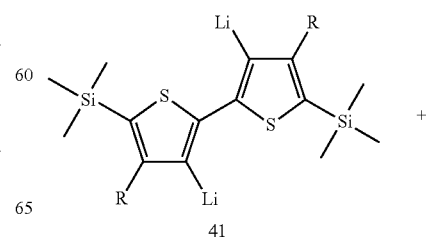

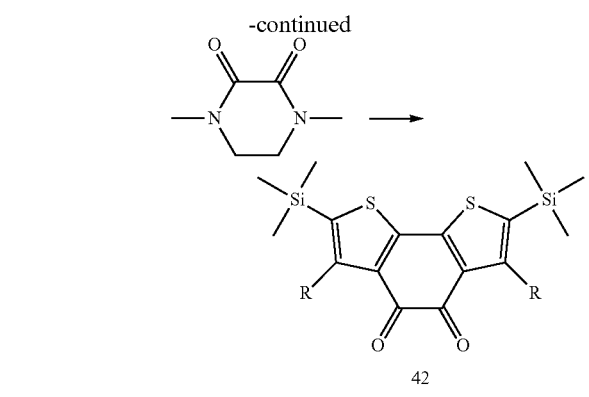

a) A solution of 9.37 g 3,3'-dibromo-5,5'-di-trimethylsilyl-2,2'-dithiophene (41) in 150 ml dry THF is cooled to −40° C. 16 ml butyl lithium (2.7 M in heptane) are added at once and the resulting solution is stirred for 15 minutes at −20° C. 3.20 g of 1,4-Dimethyl-piperazine-2,3-dione are added in one portion and the reaction mixture is allowed to warm to room temperature and stirred for an additional hour at this temperature. The reaction mixture is quenched by adding 50 ml 1 N HCl. The phases are separated and the organic phase is washed twice with brine and dried over sodium sulphate. Evaporation of the solvent affords a red residue, which is suspended in hexane. The obtained slurry is stirred for 1 hour and then filtered. The filter cake is washed with hexane and dried under vacuum. Affords 3.4 g (46% of th.) of the title compound 42 as a dark red powder. $^1$H-NMR: δ (ppm) 0.00 (s, 18H), 7.23 (s, 2H); $^{13}$C-NMR: δ (ppm) 0.00, 134.53, 136.08, 142.68, 148.47, 175.31

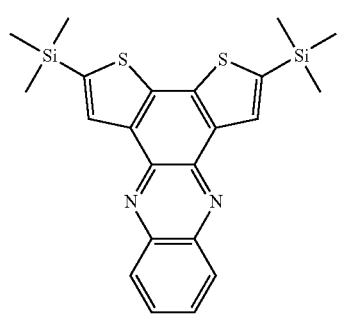

43

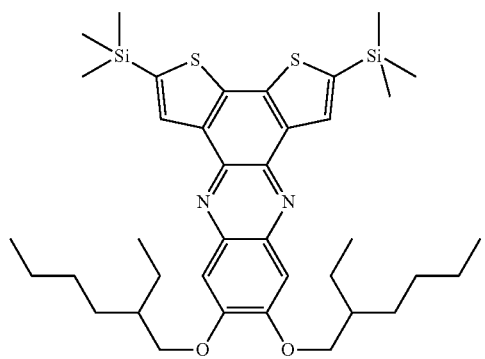

44 b) By reacting the above product 42 with o-diaminobenzene, the following compound 43 is obtained; using 1,2-di- amino-4,5-di(2-ethylhexyloxy)-benzene instead of o-di-aminobenzene yields 44. General procedure: 10 mmol 42 and 10 mmol of the aromatic ortho-diamine are dissolved in 50 ml of ethanol and refluxed for 2 hours. After cooling to 0° C. the yellow precipitate is filtered and washed with cold ethanol and dried in a vacuum oven affording the corresponding quinoxaline 43 or 44.

NMR-spectrum of 43: $^1$H-NMR: δ (ppm) 0.20 (s, 18H), 7.47 (dd, 2H), 7.94 (dd, 2H), 8.17 (s, 2H); $^{13}$C-NMR: δ (ppm) 0.00, 129.08, 131.48, 135.64, 139.82, 140.01, 140.45, 141.26

45

46

To a solution of 43 or 44 in 100 ml THF, 2 equivalents of N-bromo-succinimide are added in one portion and the reaction mixture is heated to 40° C. and stirred at this temperature for 16 hours. The solvent is then evaporated and residue is washed several times with water and then recrystallized from ethanol. The corresponding quinoxaline 45 or 46 in 60-80% yield.

NMR-spectrum of 46: $^1$H-NMR: δ (ppm) 0.98 (t, 6H), 1.06 (t, 6H), 1.42 (m, 8H), 1.62 (m, 8H), 1.96 (m, 2H), 4.13 (d, 4H), 7.19 (s, 2H), 7.97 (s, 2H)

$^{13}$C-NMR: δ (ppm) 23.15, 24.09, 24.12, 29.18, 30.73, 30.74, 39.34, 71.58, 105.65, 112.51, 126.93, 133.24, 134.48, 135.53, 139.87, 154.10

EXAMPLE 22

Synthesis of Building Block 49

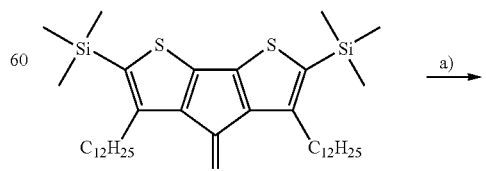

25

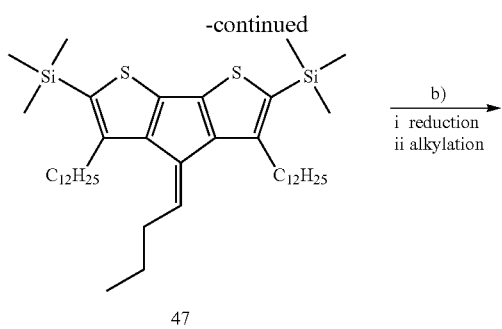

47

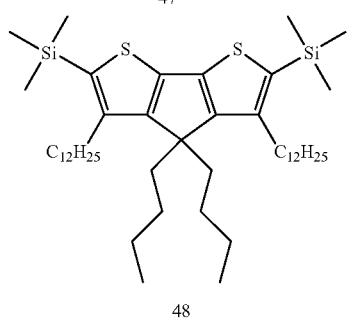

48

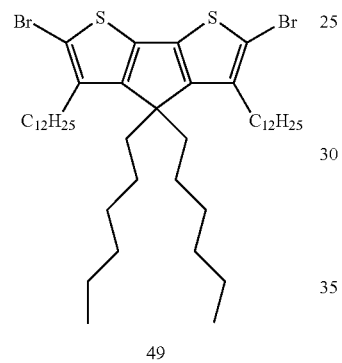

49

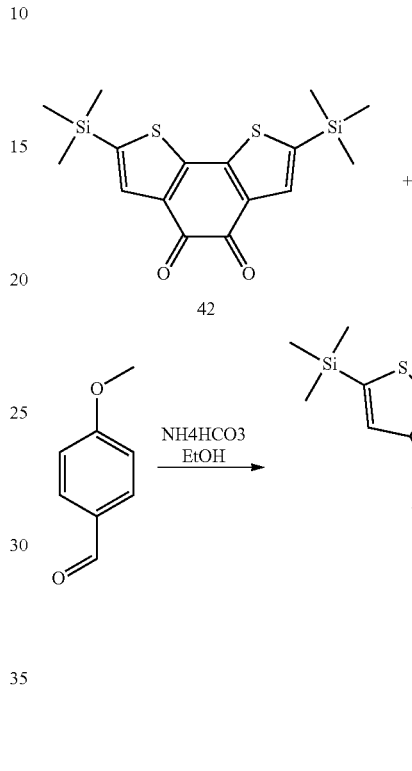

42

50

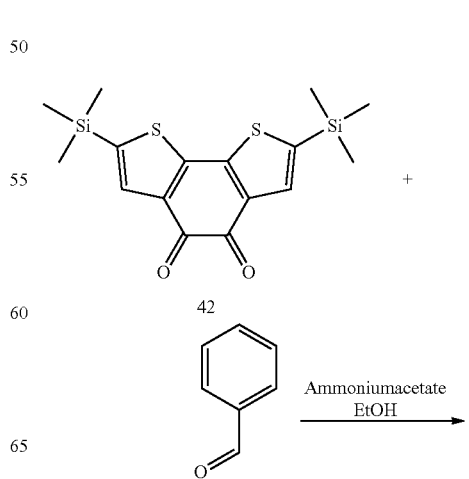

42 a) A solution of 0.5 g 25 in 5 ml THF is treated at −20° C. with 1.1 eq. butyl lithium and then slowly warmed to 0° C. The reaction is quenched by the addition of 1.1 eq. trifluoro acetic anhydride and stirred for an additional hour at room temperature.

10 ml tert.butylmethylether are added the the reaction mixture is washed with sodium bicarbonate and brine. The organic phase is separated and dried over sodium sulphate and evaporated to dryness. The residue is dissolved in 5 ml DMSO and 0.1 ml trifluoroacetic acid and stirred for 5 hours at 70° C., cooled down and poured onto a saturated sodium bicarbonate solution. The aqueous slurry is extracted twice with tert.butyl-methylether, the combined organic phases are washed with brine, dried over sodium sulphate and evaporated to dryness. Afford 0.35 g 47 as a greyish-white solid.

b) A solution of the product from above in toluene is treated with 3 eq. Red-Al (1 M in THF) and stirred at 80° C. for 2 hours. After cooling down the reaction mixture is subsequently washed with diluted HCl and brine. The organic phase is dried over sodium sulphate and evaporated to dryness.

The residue from above is dissolved in DMSO and, after the addition of 1.5 eq. butyl bromide, 5 eq. KOH and a catalytical amount of KI, stirred for 16 hours at room temperature. The reaction mass is poured onto diluted HCl and the aqueous slurry is extracted twice with hexane. The combined organic phases are washed with brine, dried over sodium sulphate and evaporated to dryness. The residue is further purified by flash chromatography affording 0.29 g 48 as a white solid.

c) Bromination according to the method described in the last step of example 11d yields 49.

$^1$H-NMR: δ (ppm) 0.81 (2×t, 12H), 0.9 (m, 4H), 1.1-1.3 (m, 46H), 1.48 (m, 4H), 1.78 (m, 4H), 2.63 (dd, 4H)

EXAMPLE 23

To 2.00 g (5.5 mmol) of 42 in 10 ml ethanol (abs) 1 ml (8.23 mmol) anisaldehyd and 2.17 g (27.42 mmol) ammoniumhydrocarbonate is added. The reaction mixture is heated at reflux under nitrogen overnight, cooled to 25° C., the product is filtered off and washed with ethanol (yield: 1.66 g (63%)).

EXAMPLE 24

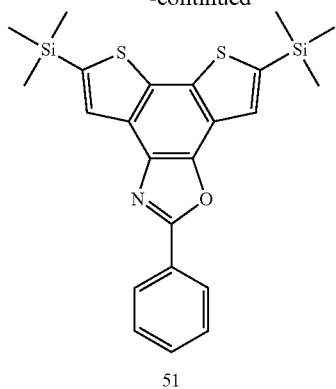

51

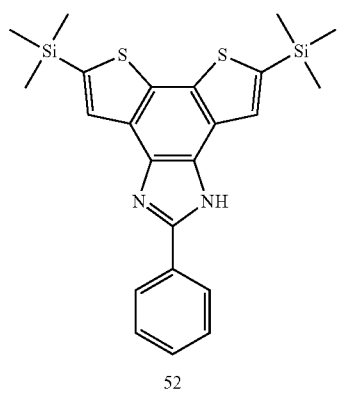

52

To 0.25 g (0.7 mmol) of 42 in 6 ml ethanol (abs) 0.11 g (1.0 mmol) benzaldehyde and 0.26 g (3.43 mol) ammonium acetate is added. The reaction mixture is heated at reflux under nitrogen overnight, cooled to 25° C., the products are filtered off and separated by column chromatography using a flash master (eluent heptane:ethyl acetate 5:1) (yield 51: 0.05 g (17%); yield 52: 0.24 g (83%)).

EXAMPLE 25

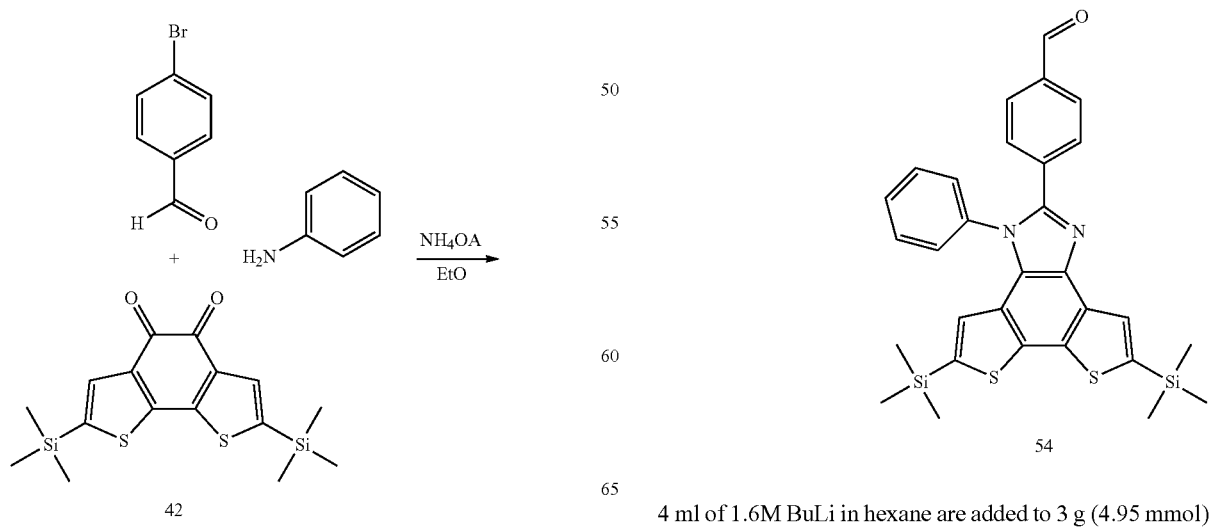

42

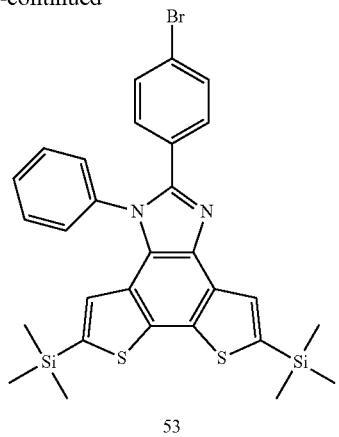

53

To 4.00 g (11.0 mmol) 42 in 80 ml acetic acid 2.23 g (12.1 mmol) 4-bromobenzaldehyde, 1.17 g (12.6 mmol) aniline and 3.38 g (43.9 mmol) ammonium acetate are added. The reaction mixture is stirred at 130° C. under nitrogen for 45 min., cooled to 25° C., and the product is filtered off and washed with AcOH/MeOH. (yield: 4.5 g (67.8%)).

EXAMPLE 26

53  1. BuLi, THF  2. DMF →

54

4 ml of 1.6M BuLi in hexane are added to 3 g (4.95 mmol) of the product of example 25 dissolved in 30 ml dry THF at −78° C. The reaction mixture is stirred for 1 h and 1.9 g (24.8 mmol) of dry DMF are added and allowed to warm to room temperature. The reaction is quenched with 0.5M HCl and the product is purified with column chromatography on silica gel with heptane:ethyl acetate (4:1) as an eluent (yield: 1.45 g (53%)).

EXAMPLE 27

EXAMPLE 28

Synthesis of Polymer 101

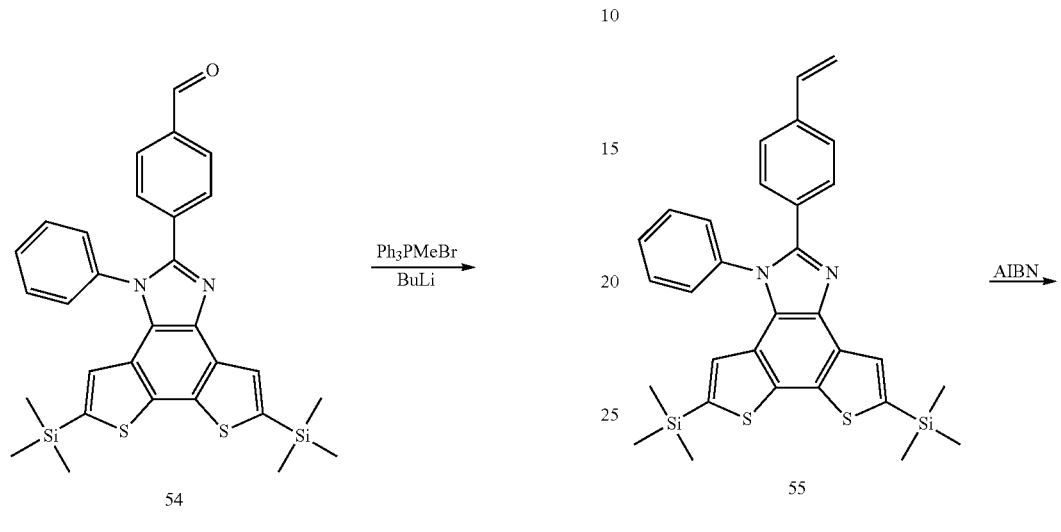

1.8 ml 1.6M BuLi in hexane (2.9 mmol) is added to 1 g of methyltriphenylphosphine bromide in 13 ml THF at 0° C. and stirred for 1 h. 1.13 g (2 mmol) of the product of example 26 in 5 ml THF is added and stirred for 1h at 0° C. Reaction mixture is wormed to RT and quenched with water. Product is extracted with ethyl acetated and purified by column chromatography with hexane:ethyl acetate as an eluent (yield: 0.81 g (73%)).

0.44 g of the product of example 27 and 0.025 g of 2,2'-azobisisobutyronitrile (AIBN) are dissolved in 1.8 ml toluene, degassed and stirred at 80° C. for 24 h. The polymer is purified by multiple precipitation in methanol (yield: 0.29 g (65%); $M_W$=22 000, PDI=3.1).

HOMO=−5.7 eV, LUMO=−2.4 eV, QY=14%

EXAMPLE 29

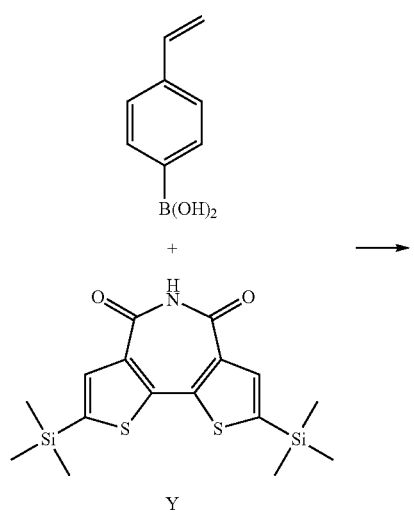

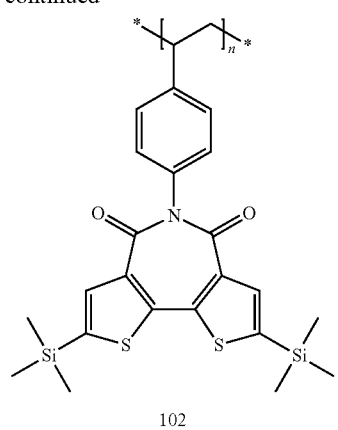
102

40 mg of product example 29 and 2 mg of 2,2'-azobisisobutyronitrile (AIBN) are dissolved in 0.18 ml toluene, degassed and stirred at 80 °C for 24 h. The polymer is purified by multiple precipitation in methanol (yield: 0.29 g (65%); Mw=27 600, PDI=2.8).

LUMO=−2.7 eV

EXAMPLE 31

Synthesis of Building Block 57

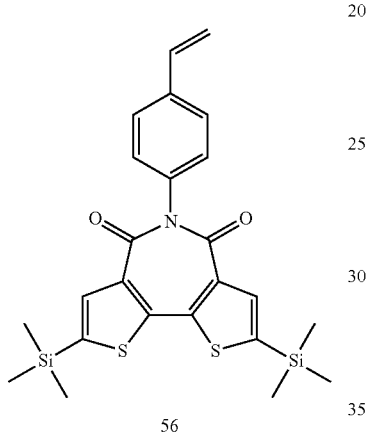

0.2g (0.53 mmol) of compound Y, 0.1 g (0.63 mmol) styrene boronic acid, 0.1 g (0.5 mmol) cupper (II) acetate and 200 mg of Molsieves 4A is stirred at 40° C. in CH2Cl2: pyridine for 3 days. Solvent is evaporated and product purified my column chromatography with heptane:ethylacetate (6:1) as en eluent. (Yield 41 mg (16%))

EXAMPLE 30

Synthesis of Polymer 102

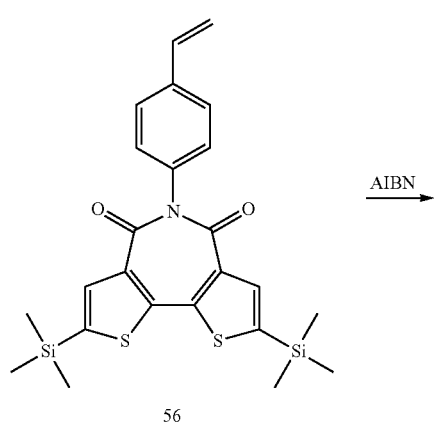

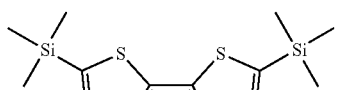

1.82 g (5 mmol) of 42 (example 21) and 0.94 g (5 mmol) of 2-amino-4-bromoaniline is refluxed overnight in 10 ml Ethanol, cooled down to RT and product is filtered off. Yield 2.4 g (93%) of product 57.

EXAMPLE 32

Synthesis of Building Block 58

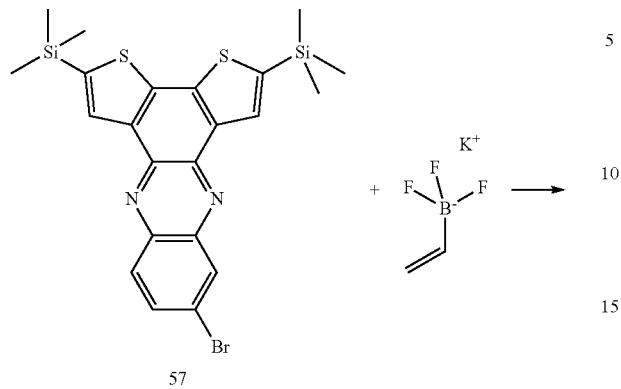

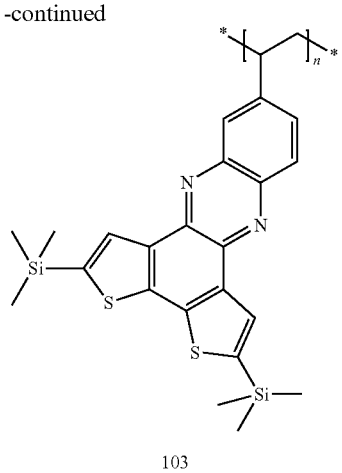

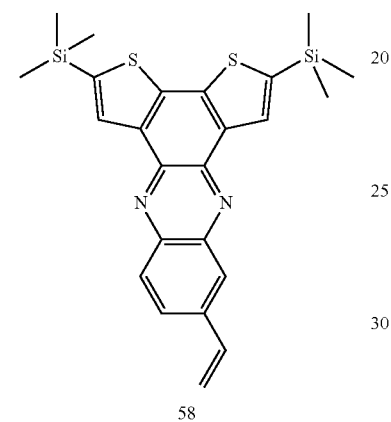

2.4 g (4.65 mmol) of product 57, 0.93 g (6.97 mmol) potassium vinyltrifluoroborate, 0.42 g (0.465 mmol) tris(dibenzylideneacetone)dipalladium(0), 6.7 g (23.25 mmol) tri-t-butylphosphonium tetrafluoroborate are mixed in 20 ml THF, degassed and heated to 50° C. Degassed aqueous solution of potassium phosphate is added and reaction mixture is stirred at reflux for 3 h. Product is purified by column chromatography with hexane:ethyl acetate (1:20). Yield 1.3 g (59.1%) of product 58.

EXAMPLE 33

Synthesis of Polymer 103

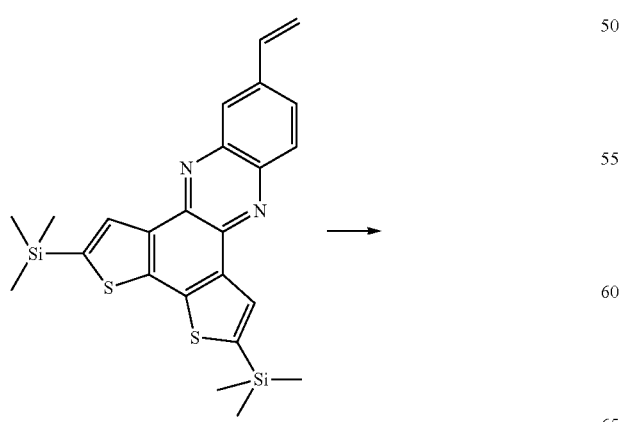

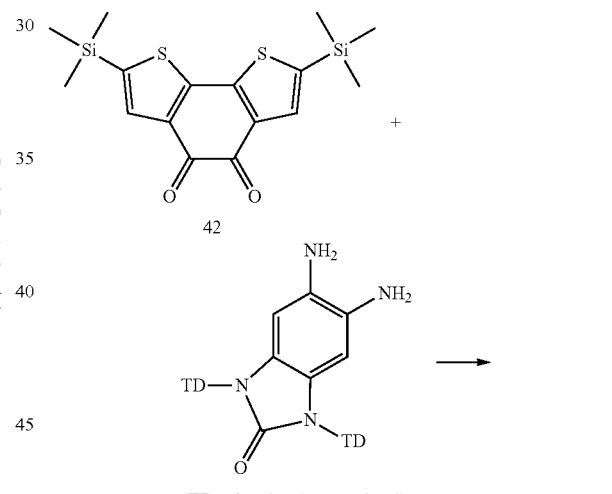

1 g of the product 58 of example 32 and 0.05 g of 2,2'-azobisisobutyronitrile (AIBN) are dissolved in 5 ml toluene, degassed and stirred at 80° C. for 24 h. The polymer is purified by multiple precipitation in methanol (yield: 0.65 g (65%); $M_w$=22 000, PDI=3.1).

HOMO=−5.7 eV, LUMO=−3.0 eV

EXAMPLE 34

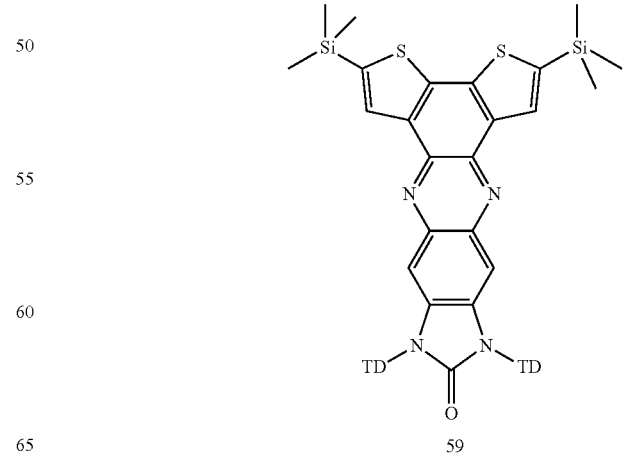

(TD = 2-n-decyl-n-tetradecyl)

10 mmol of 42 (example 21) and 10 mmol of the substituted 2-amino-aniline shown is refluxed for 2 hours in 50 ml Ethanol, cooled down to 0° C., and the yellow precipitate is filtered off, washed with cold ethanol and dried under vacuum, yielding product 59.

EXAMPLE 35

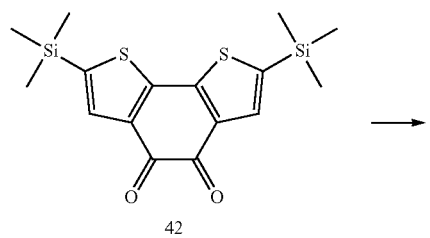

42

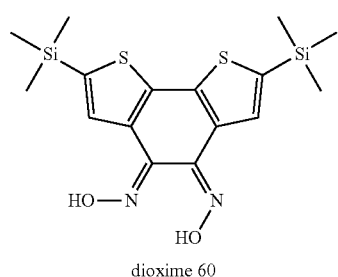

dioxime 60

10 g of the orthoquinone 42 and 10 g hydroxylamine are refluxed in 20 ml pyridine and 80 ml ethanol for 2 hours. The solvents are evaporated and the orange-red residue is suspended in 100 ml water for 3 hours. The product is isolated by filtration, extensively washed with water and dried in a vacuum oven affording 10.3 g 60 as a reddish-orange solid.

EXAMPLE 36

The product 60 as obtained in example 35 is suspended in 100 ml ethanol at 0° C. A solution of 25 g SnCl2 in 50 ml HCl conc. is added in one portion (exotherm). The reaction mixture is refluxed for 2-3 hours, cooled to 0° C. and filtered. The filter cake is washed with water and ethanol and suspended in 50 ml saturated aqueous NaHCO3 and 50 ml TBME. The organic phase is separated and washed with brine. Evaporation of the solvent affords 5.1 g 61 as beige powder.

(if 1 N HCl (instead of HCl conc.) is used, the TMS-groups are not cleaved)

EXAMPLE 37

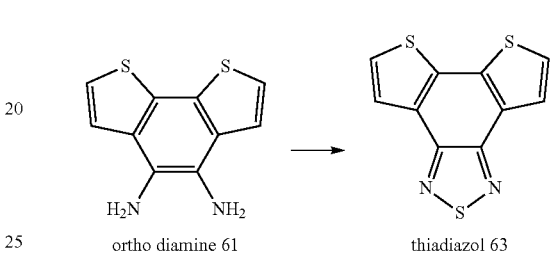

1 g of diamine 61 and 1.4 g of triethylamine are dissolved in 10 ml methylene chloride at 0° C. 1.6 g thionyl chloride is added dropwise and the reaction mixture is stirred for 1 hour at room temperature and 5 hours at reflux. The reaction is quenched by adding 10 ml water and stirred for 30 minutes. The organic phase is separated and washed with water. After evaporation of the solvent the residue is purified by chromatography affording 0.45 g 63 as yellowish powder.

EXAMPLE 38

1 g of diamine 62 and 1 g orthoquinone 42 in 10 ml ethanol are refluxed for 4 hours. After cooling to 0° C. the yellow precipitate is filtered and washed with cold ethanol and dried in a vacuum oven affording quinoxaline 64 in 70% yield:

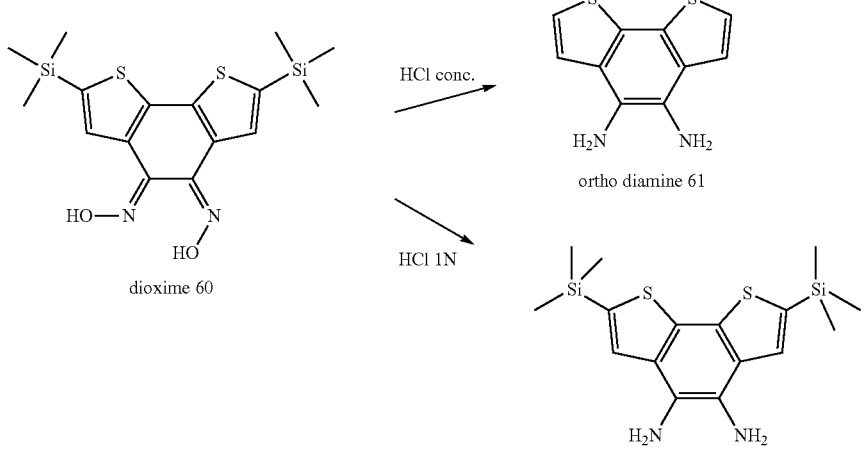

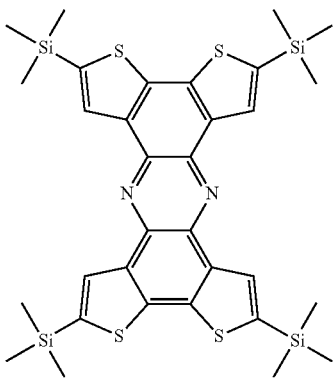

64

Several polymers can be synthesized using the above described building blocks using Suzuki polymerization conditions (Cf. Example 1).

Therefore, all described building blocks containing a trimethyl-silyl protecting group such as 33, 40, 42, 50, 51, 52 and 53 can be transformed to the corresponding dibromide using similar conditions of example 11d. These corresponding dibromides and the already described dibromide 26, 27, 28, 30, 32, 35, 39, 45, 46 and 49 can used as monomers in combination with a bisboronic ester to form polymers claimed by this invention.

All these dibromides themselves can be converted into bis boronic esters using known methods. These corresponding bis-boronic esters can then be used as momomers in combination of with the dibromides as described above to form polymers claimed by this invention.

Examples for such polymers are those of the following examples 40 and 41.

EXAMPLE 39

Compound 59 (example 34) is converted into the corresponding dibromo compound 65 in analogy to the method of example 21 (preparation of compounds 45 and 46).

EXAMPLE 40

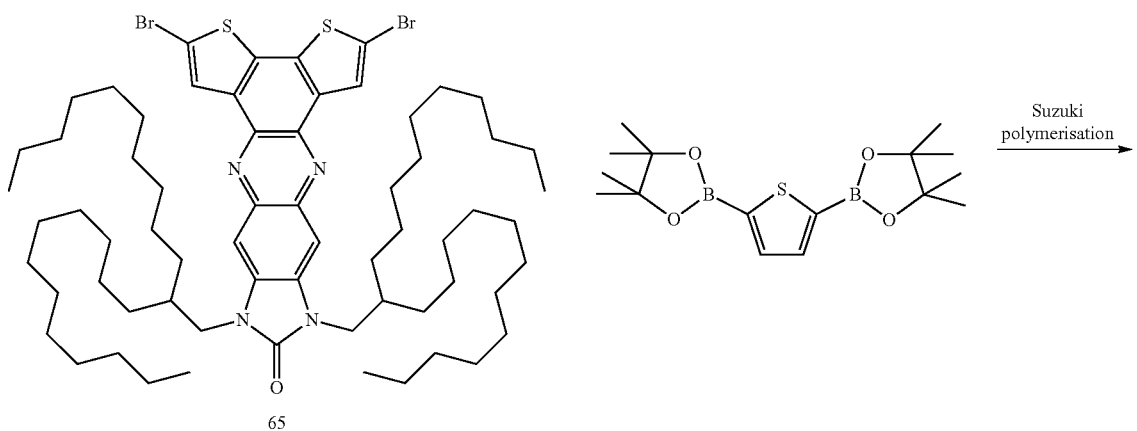

65

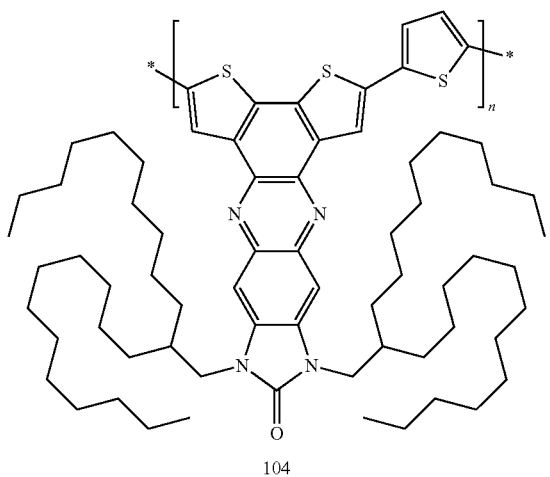

104

In a three necked flask, 0.54 g of potassium phosphate (K₃PO₄) dissolved in 5 ml of water (previously degassed) is added to a degassed solution of 1.0 g of compound 65, 0.28 g of 2,5-thiopheneboronic acid bis(pinacol) ester, 11.7 mg of tri-tert-butylphosphonium tetrafluoroborate ((t-Bu)₃P*HBF₄) and 23.3 mg of tris(dibenzylideneacetone) dipalladium (0) (Pd₂(dba)₃) in 25 ml of tetrahydrofuran. The reaction mixture is heated at reflux temperature for two hours. Subsequently, 18 mg bromo-thiophene and, 20 minutes later, 24 mg of thiophene-boronic acid pinacol ester are added to stop the polymerisation reaction. The reaction mixture is cooled to room temperature and precipitated in methanol. The residue is purified by soxhlet extraction using pentane and cyclohexane and the polymer is then extracted with THF to give 0.62 g of a dark powder. Mw=19'800, Polydispersity=1.6 (measured by HT-GPC).

EXAMPLE 41

In a three necked flask, 0.54 g of potassium phosphate (K₃PO₄) dissolved in 5 ml of water (previously degassed) is added to a degassed solution of 1.0 g of compound 65, 0.32 g of 4,7-bis-(4,4,5,5-tetramethyl-[1,3,2]dioxaborolan-2-yl)-3,4-benzo[1,2,5]thiadiazole, 11.7 mg of tri-tert-butylphosphonium tetrafluoroborate ((t-Bu)₃P*HBF₄) and 23.3 mg of tris(dibenzylideneacetone) dipalladium (0) (Pd₂(dba)₃) in 25 ml of tetrahydrofuran. The reaction mixture is heated at reflux temperature for two hours. Subsequently, 18 mg bromothiophene and, 20 minutes later, 24 mg of thiophene-boronic acid pinacol ester are added to stop the polymerisation reaction. The reaction mixture is cooled to room temperature and precipitated in methanol. The residue is purified by soxhlet extraction using pentane and the polymer is then extracted with cyclohexan to give 0.81 g of a dark powder. Mw =18'100, Polydispersity=1.6 (measured by HT-GPC).

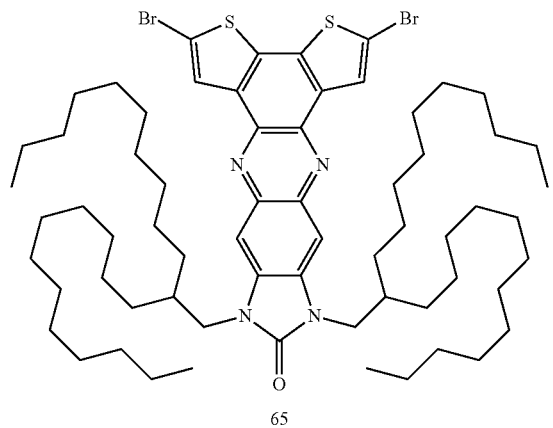

65

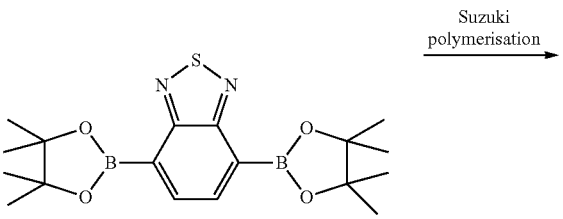

Suzuki polymerisation →

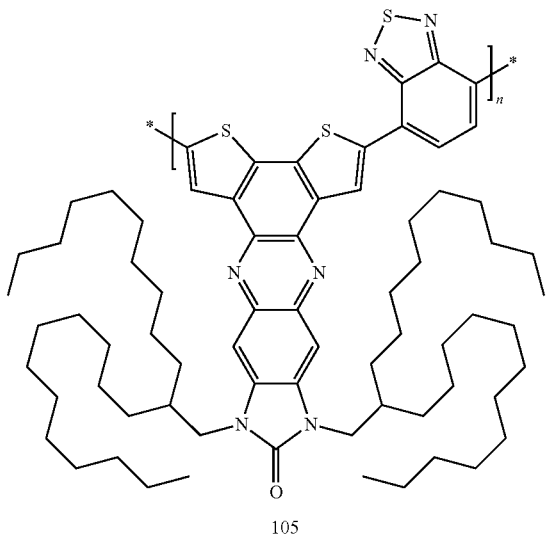

105

EXAMPLE 42

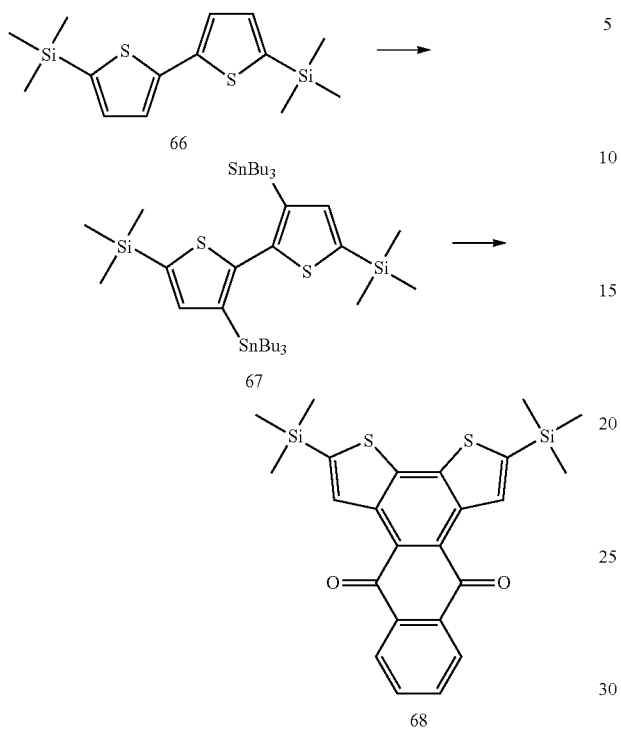

a) 38.1 g of 66 are dissolved in 300 ml THF, the mixture is then cooled to <−30° C. and 100 ml of Butyllithium (2.7M) are added. After stirring for 1 h at room temperature, the reaction mixture is cooled to −78° C., then 91.9 g Tri-n-butyltinchloride is added slowly. The reaction mixture is stirred for 2 hours at −78° C. and then heated to room temparture. The reaction mixture is then poured into an mixture of hydrochloric acid/ ice; the aqueous slurry is extracted twice with tert.butyl-methylether, the combined organic phases are washed with brine, dried over sodium sulphate and evaporated to dryness, affording 67 in good yield.

b) 10 g of 67 and 4.26 g of 2,3-dibromo-2,3-dihydro-1,4-naphthoquinone are mixed in 100 ml toluene and the solution is degassed. 0.2 g of tris(dibenzylideneacetone) dipalladium(0) and 0.14 g of triphenylarsine are added. The reaction mixture is heated to 120° C. overnight. The reaction mixture is then filtered over silicagel, precipated in hexane and filtered, to obtain 68 in good yield.

EXAMPLE 43

Organic Field Effect Transistor (OFET)

Bottom-gate thin film transistor (TFT) structures with p-Si gate (10 cm) are used for all experiments. A high-quality thermal $SiO_2$ layer of 300 nm thickness serves as gate-insulator of $C_i$=32.6 $nF/cm^2$ capacitance per unit area. Source and drain electrodes are patterned by photolithography directly on the gate-oxide. Gold source drain electrodes defining channels of width W=10 mm and varying lengths L=4, 8, 15, 30 μm are used. Prior to deposition of the organic semiconductor the $SiO_2$ surface is derivatized either with hexadimethylsilazane (HMDS) by exposing to a saturated silane vapour at 160° C. for 2 hours or by spin coating the HMDS at a spinning speed of 800 rpm (rounds per minute) for about a minute, or by treating the substrate at 60° C. with a 0.1 M solution of octadecyltrichlorosilane (OTS) in toluene for 20 minutes. After rinsing with iso-propanol the substrates are dried.

The semiconductor thin film is prepared either by spin-coating or drop casting the compound as identified in the following table in a 0.5% (w/w) solution in ortho-dichlorobenzene. The spin coating is accomplished at a spinning speed of 1000 rpm (rounds per minute) for about 60 seconds in ambient conditions. The devices are evaluated as-deposited and after drying at 120° C. for 15 minutes.

The transistor performance is measured on an automated transistor prober (TP-10). From a linear fit to the square root of the saturated transfer characteristics, field effect mobility and on/off current ratio are determined. Characteristic data are compiled in the following table.

TABLE

OFET Characteristics

| Sample Compound | Field Effect Mobility | On/off Current Ratio | Threshold Voltage |
|---|---|---|---|
| 104 | $2.1 \times 10^{-3}$ $cm^2/Vs$ | $1.8 \times 10^5$ | −12 V |
| 105 | $1.6 \times 10^{-4}$ $cm^2/Vs$ | $5.3 \times 10^5$ | −8 V |

The invention claimed is:

1. A compound of formula (I):

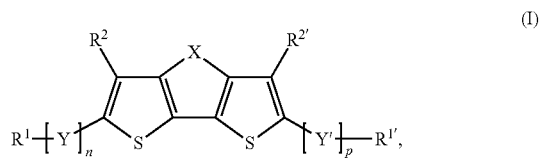

wherein:

X is a divalent linking group selected from the group consisting of

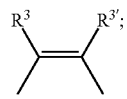

$R^1$ and $R^{1'}$ independently of each other are a substituent, a halogen or $SiR^6R^4R^5$;

$R^2$ and $R^{2'}$ are optionally the same or different and are selected from the group consisting of hydrogen, a halogen, a $C_1$-$C_{25}$alkyl, a $C_7$-$C_{25}$arylalkyl or a $C_1$-$C_{25}$alkoxy, each of which is unsubstituted or substituted;

$R^3$ and $R^{3'}$ together with the carbon atoms to which they are attached, complete a 5- or 6-membered unsubstituted or substituted hydrocarbon ring having a structure:

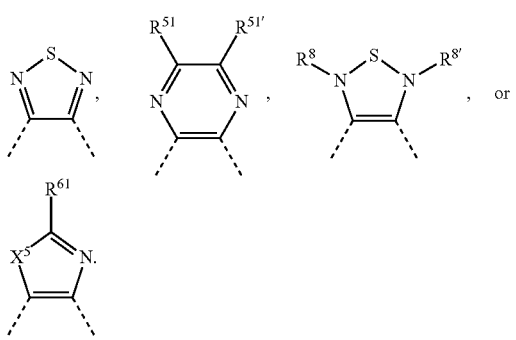

, or

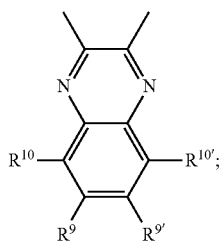

Y and Y' independently are selected from the group consisting of

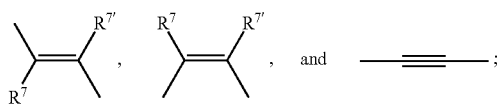

n and p are both 0;

$R^3$ and $R^{3'}$ optionally together form a bridging group

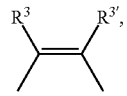

$R^4$, $R^5$, $R^6$ independently are a $C_1$-$C_6$alkyl;

$R^7$ and $R^{7'}$ independently represent H or the substituent, or vicinal $R^7$ and $R^{7'}$, together with carbon atoms to which they are attached, complete a 5-membered unsubstituted or substituted heterocyclic ring comprising at least one heteroatom selected from the group consisting of N, O and S;

$R^9$, $R^{9'}$, $R^{10}$ and $R^{10'}$ independently are hydrogen, wherein at least one of neighbouring residues $R^9$ and $R^{9'}$, or $R^9$ and $R^{10}$, $R^{9'}$ and $R^{10'}$, or both, together with carbon atoms to which they are attached, complete a 5-membered unsubstituted or substituted heterocyclic ring comprising at least one heteroatom selected from the group consisting of N, O and S;

the optional substituent is independently selected from the group consisting of a $C_1$-$C_8$alkyl, a hydroxyl group, a mercapto group, a $C_1$-$C_8$alkoxy, a $C_1$-$C_8$alkylthio, a halogen, a halo-$C_1$-$C_8$alkyl, a cyano group, a carbamoyl group, a nitro group and a silyl group;

$X^5$ is —O— or —$NR^8$—;

$R^8$ and $R^{8'}$ are independently of each other hydrogen, a $C_6$-$C_{18}$aryl, a $C_6$-$C_{18}$aryl which is substituted by a $C_1$-$C_{18}$alkyl or a $C_1$-$C_{18}$alkoxy; a $C_1$-$C_{25}$alkyl which may optionally be interrupted by one or more oxygen or sulfur atoms, or a $C_7$-$C_{25}$arylalkyl;

$R^{51}$ and $R^{51'}$ are independently of each other hydrogen, a halogen, a $C_1$-$C_{25}$alkyl which may optionally be interrupted by one or more oxygen or sulfur atoms, a $C_6$-$C_{24}$aryl which may optionally be substituted one to three times with a $C_1$-$C_8$alkyl and/or a $C_1$-$C_8$alkoxy, a $C_7$-$C_{25}$arylalkyl, CN, or a $C_1$-$C_{25}$alkoxy, or $R^{51}$ and $R^{51'}$ together form a ring; and $R^{61}$ is H, a $C_1$-$C_{18}$alkyl which may optionally be interrupted by one or more oxygen or sulfur atoms, a $C_1$-$C_{18}$perfluoroalkyl, a $C_6$-$C_{24}$aryl which may optionally be substituted one to three times with a $C_1$-$C_8$alkyl and/or a $C_1$-$C_8$alkoxy, a $C_2$-$C_{20}$heteroaryl which may optionally be substituted one to three times with a $C_1$-$C_8$alkyl and/or a $C_1$-$C_8$alkoxy, or CN.

2. The compound of claim 1, wherein:

$R^1$ and $R^{1'}$ are independently of each other halogen or $SiR^6R^4R^5$;

$R^2$ and $R^{2'}$ are optionally the same or different and are selected from the group consisting of halogen, hydrogen, a $C_1$-$C_{25}$alkyl, a $C_7$-$C_{25}$arylalkyl or a $C_1$-$C_{25}$alkoxy, each of which is unsubstituted or substituted;

X is

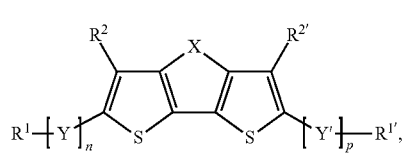

wherein $R^3$ and $R^{3'}$ together form the ring structure;

$R^4$, $R^5$, $R^6$ independently are a $C_1$-$C_6$alkyl;

$R^9$ $R^{9'}$, $R^{10}$ and $R^{10'}$ independently are hydrogen; and the optional substituent is independently selected from the group consisting of a $C_1$-$C_8$alkyl, a hydroxyl group, a mercapto group, a $C_1$-$C_8$alkoxy, a $C_1$-$C_8$alkylthio, a halogen, a halo-$C_1$-$C_8$alkyl, a cyano group, a carbamoyl group, a nitro group and a silyl group.

3. The compound of claim 1, wherein:

$R^1$ and $R^{1'}$ are independently of each other halogen or $SiR^6R^4R^5$;

$R^2$ and $R^{2'}$ are optionally the same or different and are selected from the group consisting of H, a $C_1$-$C_{25}$alkyl, a $C_7$-$C_{25}$arylalkyl or a $C_1$-$C_{25}$alkoxy; and $R^4$, $R^5$, $R^6$ independently are a $C_1$-$C_6$alkyl.

4. A compound of formula (I):

(I)

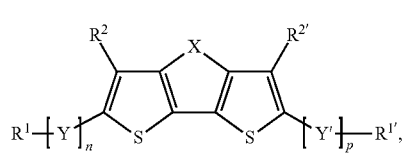

wherein:

X is a divalent linking group selected from the group consisting of

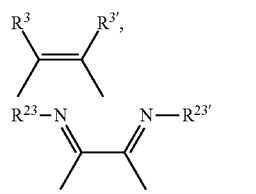

and

-continued

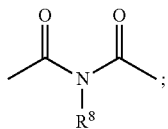

R¹ and R¹' are independently of each other H, halogen or SiR⁶R⁴R⁵;
R² and R²' independently are H or $C_1$-$C_{18}$alkyl;
R³ and R³' together form a ring closing structure selected from the group consisting of S—CH=N, O—CH=N, and NR—CH=N, wherein a CH moiety is substituted, or

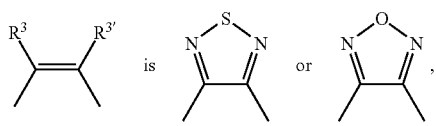

or R³ and R³' together form a bridging group:

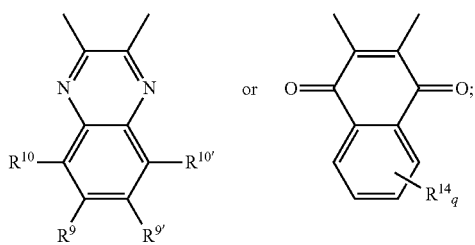

R⁴, R⁵, R⁶ independently are $C_1$-$C_8$alkyl groups;
n and p are 0;
Y and Y' independently are selected from the group consisting of

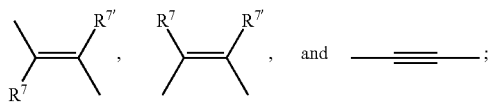

neighbouring residues R⁴ and R⁵ are optionally further interlinked to form a divalent hydrocarbon residue comprising 4 to 25 carbon atoms optionally substituted, interrupted, or both;
R⁷ and R⁷' independently represent H or the substituent, or vicinal R⁷ and R⁷', together with carbon atoms to which they are attached, complete a 5-membered unsubstituted or substituted heterocyclic ring comprising at least one heteroatom selected from the group consisting of N, O, and S;
R²³ and R²³' each represent an alkyl group, a hydroxyl or an alkoxy group;
R⁸ is substituted phenyl;
R⁹, R⁹', R¹⁰ and R¹⁰' independently are hydrogen and one or more of neighbouring residues R⁹ and R⁹' together form a moiety N—CO—N whose nitrogen atoms are substituted,
or
R⁹ and R¹⁰, and R⁹' and R¹⁰' each, together with carbon atoms to which they are attached, complete an unsubstituted or substituted thienyl ring;
q is 0, 1, 2, 3 or 4;
R14, if present, is the substituent;
the substituent, if present, is independently selected from the group consisting of a halogen, $C_1$-$C_{25}$alkyl, SiRR'R", vinyl, allyl, and phenyl, and if bonding to a non-aromatic carbon or to a sulphur, the substituent is optionally oxo, wherein R, R', R" independently are selected from the group consisting of $C_1$-$C_8$alkyl, and phenyl, and R is optionally a hydrogen, and each phenyl is unsubstituted or substituted by $C_1$-$C_4$alkyl, $C_1$-$C_4$alkoxy, CHO, vinyl, allyl, allyloxy, acryloyloxy, methacryloyloxy, or halogen.

5. A semiconductor device, comprising the compound according to claim 1.

6. The semiconductor device of claim 5, comprising the compound of the formula (I) as a layer having a thickness from the range 5 to 1000 nm, on a rigid or flexible solid substrate.

7. An organic semiconductor material, layer or component, comprising the compound of claim 1.

8. A process for preparing an organic semiconductor device, the process comprising:
applying a solution and/or dispersion of the compound of claim 1, in an organic solvent, to a substrate; and
removing the organic solvent.

9. An article, comprising the compound of claim 1, wherein the article is selected from the group consisting of a charge-transport material, a semiconducting material, an electrically conducting material, a photoconducting material, a light emitting material, a surface-modifying material, an electrode material in a battery, an alignment layer, an organic field effect transistor, an integrated circuit, a thin film transistor, a display, an RFID tag, an electro- or photoluminescent device, a backlight of a display, a photovoltaic or sensor device, a charge injection layer, a photodiode, a Schottky diode, a memory device, a planarising layer, an antistatic, a conductive substrate or pattern, a photoconductor, and an electrophotographic application or recording material.

10. The compound of claim 4, wherein q is 0.

* * * * *